US007632228B2

(12) United States Patent
Brauker et al.

(10) Patent No.: US 7,632,228 B2
(45) Date of Patent: *Dec. 15, 2009

(54) MEMBRANE FOR USE WITH IMPLANTABLE DEVICES

(75) Inventors: James H. Brauker, San Diego, CA (US); Mark C. Shults, Madison, WI (US); Mark A. Tapsak, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 1280 days.

This patent is subject to a terminal disclaimer.

(21) Appl. No.: 10/768,889

(22) Filed: Jan. 29, 2004

(65) Prior Publication Data

US 2004/0186362 A1 Sep. 23, 2004

Related U.S. Application Data

(63) Continuation of application No. 09/916,386, filed on Jul. 27, 2001, now Pat. No. 6,702,857.

(51) Int. Cl.
*A61B 5/00* (2006.01)
*A61F 2/02* (2006.01)
*G01N 27/40* (2006.01)

(52) U.S. Cl. ....................... 600/309; 600/345; 600/347; 623/23.76; 204/403.07; 204/415

(58) Field of Classification Search ................. 600/309, 600/345, 347; 204/403.01, 403.06, 403.07, 204/403.1, 403.11, 403.14, 415
See application file for complete search history.

(56) References Cited

U.S. PATENT DOCUMENTS 3,775,182 A 11/1973 Patton et al.

(Continued)

FOREIGN PATENT DOCUMENTS

EP 0 098 592 1/1984

(Continued)

OTHER PUBLICATIONS

Armour, et al. Dec. 1990. Application of Chronic Intravascular Blood Glucose Sensor in Dogs. Diabetes 39:1519-1526.

(Continued)

*Primary Examiner*—Eric F Winakur
(74) *Attorney, Agent, or Firm*—Knobbe Martens Olson & Bear LLP

(57) ABSTRACT

The present invention provides a biointerface membrane for use with an implantable device that interferes with the formation of a barrier cell layer including; a first domain distal to the implantable device wherein the first domain supports tissue attachment and interferes with barrier cell layer formation and a second domain proximal to the implantable device wherein the second domain is resistant to cellular attachment and is impermeable to cells. In addition, the present invention provides sensors including the biointerface membrane, implantable devices including these sensors or biointerface membranes, and methods of monitoring glucose levels in a host utilizing the analyte detection implantable device of the invention. Other implantable devices which include the biointerface membrane of the present invention, such as devices for cell transplantation, drug delivery devices, and electrical signal delivery or measuring devices are also provided.

45 Claims, 9 Drawing Sheets

U.S. PATENT DOCUMENTS

| | | | | |
|---|---|---|---|---|
| 3,898,984 | A | 8/1975 | Mandel et al. | |
| 3,929,971 | A | 12/1975 | Roy | 423/308 |
| 3,943,918 | A | 3/1976 | Lewis | |
| 3,964,974 | A | 6/1976 | Banauch et al. | |
| 3,966,580 | A | 6/1976 | Janata et al. | 204/403.07 |
| 3,979,274 | A | 9/1976 | Newman | 204/403.09 |
| 4,024,312 | A | 5/1977 | Korpman | |
| 4,040,908 | A | 8/1977 | Clark, Jr. | 205/778 |
| 4,073,713 | A | 2/1978 | Newman | 204/403.09 |
| 4,076,656 | A | 2/1978 | White et al. | 521/64 |
| 4,172,770 | A | 10/1979 | Semersky et al. | 205/778 |
| 4,197,840 | A | 4/1980 | Beck et al. | |
| 4,215,703 | A | 8/1980 | Willson | |
| 4,225,410 | A | 9/1980 | Pace | |
| 4,240,889 | A | 12/1980 | Yoda et al. | 204/403.09 |
| 4,253,469 | A | 3/1981 | Aslan | |
| 4,255,500 | A | 3/1981 | Hooke | |
| 4,259,540 | A | 3/1981 | Sabia | |
| 4,260,725 | A * | 4/1981 | Keogh et al. | 526/279 |
| 4,353,888 | A | 10/1982 | Sefton | 424/424 |
| 4,374,013 | A | 2/1983 | Enfors | |
| 4,388,166 | A | 6/1983 | Suzuki et al. | 204/403.05 |
| 4,403,984 | A | 9/1983 | Ash et al. | |
| 4,415,666 | A | 11/1983 | D'Orazio et al. | 204/403.11 |
| 4,418,148 | A | 11/1983 | Oberhardt | 204/403.11 |
| 4,431,004 | A | 2/1984 | Bessman et al. | 600/347 |
| 4,436,094 | A | 3/1984 | Cerami | 600/347 |
| 4,442,841 | A | 4/1984 | Uehara et al. | |
| 4,453,537 | A | 6/1984 | Spitzer | |
| 4,477,314 | A | 10/1984 | Richter et al. | |
| 4,484,987 | A | 11/1984 | Gough | 205/778 |
| 4,494,950 | A | 1/1985 | Fischell | |
| 4,506,680 | A | 3/1985 | Stokes | 607/120 |
| RE31,916 | E | 6/1985 | Oswin et al. | |
| 4,534,355 | A | 8/1985 | Potter | 600/360 |
| 4,554,927 | A | 11/1985 | Fussell | |
| 4,571,292 | A | 2/1986 | Liu et al. | |
| 4,577,642 | A | 3/1986 | Stokes | 607/120 |
| 4,650,547 | A | 3/1987 | Gough | 205/778 |
| 4,663,824 | A | 5/1987 | Kenmochi | |
| 4,671,288 | A | 6/1987 | Gough | 600/347 |
| 4,680,268 | A * | 7/1987 | Clark, Jr. | 600/347 |
| 4,686,044 | A | 8/1987 | Behnke et al. | 210/500.22 |
| 4,689,309 | A | 8/1987 | Jones | 436/95 |
| 4,702,732 | A | 10/1987 | Powers et al. | 604/20 |
| 4,703,756 | A | 11/1987 | Gough et al. | 600/347 |
| 4,711,251 | A | 12/1987 | Stokes | 607/116 |
| 4,721,677 | A | 1/1988 | Clark, Jr. | |
| 4,731,726 | A | 3/1988 | Allen | |
| 4,753,652 | A | 6/1988 | Langer et al. | 623/1.42 |
| 4,757,022 | A | 7/1988 | Shults et al. | 204/403.05 |
| 4,759,828 | A | 7/1988 | Young et al. | 205/778 |
| 4,776,944 | A | 10/1988 | Janata et al. | 204/403.08 |
| 4,781,798 | A | 11/1988 | Gough | 205/783 |
| 4,787,398 | A | 11/1988 | Garcia et al. | |
| 4,803,243 | A | 2/1989 | Fujimoto et al. | 525/100 |
| 4,805,625 | A | 2/1989 | Wyler | |
| 4,810,470 | A | 3/1989 | Burkhardt et al. | 422/56 |
| 4,823,808 | A | 4/1989 | Clegg et al. | |
| 4,852,573 | A | 8/1989 | Kennedy | |
| 4,861,830 | A | 8/1989 | Ward, Jr. | 525/92 A |
| 4,871,440 | A | 10/1989 | Nagata et al. | |
| 4,883,057 | A | 11/1989 | Broderick | |
| 4,889,744 | A | 12/1989 | Quaid | 427/2.24 |
| 4,890,620 | A | 1/1990 | Gough | 600/348 |
| 4,902,294 | A | 2/1990 | Gosserez | |
| 4,927,407 | A | 5/1990 | Dorman | |
| 4,935,345 | A | 6/1990 | Guilbeau et al. | 435/14 |
| 4,953,552 | A | 9/1990 | DeMarzo | |
| 4,963,595 | A | 10/1990 | Ward et al. | 525/415 |
| 4,970,145 | A * | 11/1990 | Bennetto et al. | 204/403.11 |
| 4,984,929 | A | 1/1991 | Rock et al. | 403/230 |
| 4,986,271 | A | 1/1991 | Wilkins | |
| 4,986,671 | A | 1/1991 | Sun et al. | 374/131 |
| 4,994,167 | A | 2/1991 | Shults et al. | 204/403.05 |
| 5,002,572 | A | 3/1991 | Picha | 623/23.74 |
| 5,007,929 | A | 4/1991 | Quaid | 623/8 |
| 5,050,612 | A | 9/1991 | Matsumura | |
| 5,059,654 | A | 10/1991 | Hou et al. | 525/54.1 |
| 5,067,491 | A | 11/1991 | Taylor et al. | |
| 5,101,814 | A | 4/1992 | Palti | 600/347 |
| 5,113,871 | A | 5/1992 | Viljanto et al. | 600/581 |
| 5,130,231 | A | 7/1992 | Kennedy et al. | |
| 5,137,028 | A | 8/1992 | Nishimura | |
| 5,165,407 | A | 11/1992 | Wilson et al. | 600/345 |
| 5,171,689 | A | 12/1992 | Kawaguri et al. | |
| 5,190,041 | A | 3/1993 | Palti | 600/347 |
| 5,222,980 | A | 6/1993 | Gealow | |
| 5,235,003 | A | 8/1993 | Ward et al. | 525/476 |
| 5,249,576 | A | 10/1993 | Golberger et al. | |
| 5,264,104 | A | 11/1993 | Gregg et al. | |
| 5,269,891 | A | 12/1993 | Colin | |
| 5,271,736 | A | 12/1993 | Picha | 623/23.74 |
| 5,282,848 | A | 2/1994 | Schmitt | |
| 5,285,513 | A | 2/1994 | Kaufman et al. | |
| 5,299,571 | A | 4/1994 | Mastrototaro | |
| 5,304,468 | A | 4/1994 | Phillips et al. | |
| 5,310,469 | A | 5/1994 | Cunningham et al. | |
| 5,314,471 | A | 5/1994 | Brauker et al. | 623/23.72 |
| 5,316,008 | A | 5/1994 | Suga et al. | |
| 5,321,414 | A | 6/1994 | Alden et al. | |
| 5,322,063 | A | 6/1994 | Allen et al. | 600/347 |
| 5,326,356 | A | 7/1994 | Della Valle et al. | 623/15.12 |
| 5,330,521 | A | 7/1994 | Cohen | |
| 5,331,555 | A | 7/1994 | Hashimoto et al. | |
| 5,340,352 | A | 8/1994 | Nakanishi et al. | 450/57 |
| 5,342,409 | A | 8/1994 | Mullett | |
| 5,343,869 | A | 9/1994 | Pross et al. | |
| 5,344,454 | A | 9/1994 | Clarke et al. | 623/23.72 |
| 5,348,788 | A | 9/1994 | White | 428/131 |
| 5,356,786 | A | 10/1994 | Heller et al. | 205/778 |
| 5,368,028 | A | 11/1994 | Palti | |
| 5,372,133 | A | 12/1994 | Esch | 600/377 |
| 5,380,536 | A | 1/1995 | Hubbell et al. | 424/497 |
| 5,384,028 | A | 1/1995 | Ito | |
| 5,387,327 | A | 2/1995 | Khan | |
| 5,390,671 | A | 2/1995 | Lord et al. | |
| 5,391,250 | A | 2/1995 | Cheney et al. | 156/268 |
| 5,397,848 | A | 3/1995 | Yang et al. | 525/477 |
| 5,411,647 | A | 5/1995 | Johnson et al. | |
| 5,417,395 | A | 5/1995 | Fowler et al. | |
| 5,421,923 | A | 6/1995 | Clarke et al. | |
| 5,428,123 | A | 6/1995 | Ward et al. | 528/28 |
| 5,431,160 | A | 7/1995 | Wilkins | 600/347 |
| 5,453,278 | A | 9/1995 | Chan et al. | 424/422 |
| 5,458,631 | A | 10/1995 | Xavier | |
| 5,462,051 | A | 10/1995 | Oka et al. | |
| 5,462,064 | A | 10/1995 | D'Angelo et al. | 600/584 |
| 5,469,846 | A | 11/1995 | Khan | 600/347 |
| 5,476,094 | A | 12/1995 | Allen et al. | 600/342 |
| 5,480,711 | A | 1/1996 | Ruefer | |
| 5,484,404 | A | 1/1996 | Schulman et al. | |
| 5,491,474 | A | 2/1996 | Suni et al. | |
| 5,494,562 | A | 2/1996 | Maley et al. | |
| 5,496,453 | A | 3/1996 | Uenoyama et al. | 205/777.5 |
| 5,497,772 | A | 3/1996 | Schulman et al. | |
| 5,507,288 | A | 4/1996 | Bocker et al. | |
| 5,513,636 | A | 5/1996 | Palti | |
| 5,529,066 | A | 6/1996 | Palti | |
| 5,531,878 | A | 7/1996 | Vadgama et al. | 205/778 |
| 5,538,511 | A | 7/1996 | Van Antwerp | |
| 5,540,828 | A | 7/1996 | Yacynych | 205/198 |
| 5,545,220 | A | 8/1996 | Andrews et al. | 623/8 |
| 5,545,223 | A | 8/1996 | Neuenfeldt et al. | 435/325 |

5,549,675 A 8/1996 Neuenfeldt et al. ......... 435/325
5,564,439 A 10/1996 Picha ...................... 604/890.1
5,568,806 A 10/1996 Cheney et al.
5,569,186 A 10/1996 Lord et al. .................... 604/67
5,569,462 A 10/1996 Martinson et al. ........... 424/424
5,571,395 A 11/1996 Park et al.
5,575,930 A 11/1996 Tietje-Girault et al.
5,578,463 A 11/1996 Berka et al.
5,582,184 A 12/1996 Erickson et al.
5,584,876 A 12/1996 Bruchman et al.
5,586,553 A 12/1996 Halili et al.
5,589,563 A 12/1996 Ward et al. .................... 528/44
5,590,651 A 1/1997 Shaffer et al.
5,593,440 A 1/1997 Brauker et al. .............. 424/423
5,593,852 A 1/1997 Heller et al. .................. 435/14
5,624,537 A 4/1997 Turner et al.
5,628,890 A 5/1997 Carter et al. ........... 204/403.05
5,640,954 A 6/1997 Pfeiffer
5,653,756 A 8/1997 Clarke et al. ............. 623/11.11
5,653,863 A 8/1997 Genshaw et al. ......... 205/777.5
5,658,330 A 8/1997 Carlisle et al. ........... 623/11.11
5,660,163 A 8/1997 Schulman et al.
5,683,562 A 11/1997 Schaffar et al.
5,686,829 A 11/1997 Girault
5,695,623 A 12/1997 Michel et al.
5,704,354 A 1/1998 Priedel et al.
5,706,807 A 1/1998 Picha ......................... 600/345
5,711,861 A 1/1998 Ward et al. .................. 600/347
5,713,888 A 2/1998 Neuenfeldt et al. ...... 604/891.1
5,733,336 A 3/1998 Neuenfeldt et al. ......... 435/325
5,741,330 A 4/1998 Brauker et al. .............. 424/423
5,743,262 A 4/1998 Lepper, Jr. et al.
5,756,632 A 5/1998 Ward et al. .................... 528/28
5,776,324 A 7/1998 Usala ......................... 600/345
5,777,060 A 7/1998 Van Antwerp ............... 528/28
5,779,665 A 7/1998 Mastrototaro et al.
5,782,912 A 7/1998 Brauker et al. .............. 424/422
5,783,054 A 7/1998 Raguse et al. .......... 204/403.08
5,787,900 A 8/1998 Butler et al.
5,791,344 A 8/1998 Schulman et al. ........... 600/347
5,795,774 A 8/1998 Matsumoto et al. .... 204/403.11
5,798,065 A 8/1998 Picha ........................ 264/46.4
5,800,420 A 9/1998 Gross
5,800,529 A 9/1998 Brauker et al. ............. 623/2.38
5,804,048 A * 9/1998 Wong et al. ............ 204/403.11
5,807,375 A 9/1998 Gross et al.
5,807,406 A 9/1998 Brauker et al. .............. 424/423
5,811,487 A 9/1998 Schulz, Jr. et al. .......... 524/862
5,820,622 A 10/1998 Gross et al.
5,833,603 A 11/1998 Kovacs et al.
5,837,728 A 11/1998 Purcell
5,840,240 A 11/1998 Stenoien et al. ............. 264/425
5,851,197 A 12/1998 Marano et al.
5,861,019 A 1/1999 Sun et al. ...................... 607/60
5,871,514 A 2/1999 Wiklund et al. ............... 607/36
5,882,494 A 3/1999 Van Antwerp .............. 600/347
5,897,578 A 4/1999 Wiklund et al. ............... 607/36
5,904,708 A 5/1999 Goedeke ...................... 607/18
5,910,554 A 6/1999 Kempe et al. ............... 526/320
5,913,998 A 6/1999 Butler et al. ................ 156/245
5,914,026 A 6/1999 Blubaugh, Jr. et al. ...... 600/347
5,917,346 A 6/1999 Gord
5,919,215 A 7/1999 Wiklund et al. ............... 607/36
5,931,814 A 8/1999 Alex et al.
5,944,661 A 8/1999 Swette et al.
5,957,854 A 9/1999 Besson et al.
5,957,903 A 9/1999 Mirzaee et al.
5,961,451 A 10/1999 Reber et al.
5,964,261 A 10/1999 Neuenfeldt et al. ......... 141/327
5,964,804 A 10/1999 Brauker et al. .............. 424/423
5,964,993 A 10/1999 Blubaugh et al.
5,965,380 A 10/1999 Heller et al. .................. 435/14
5,967,986 A 10/1999 Cimochowski et al.
5,976,085 A 11/1999 Kimball et al. ............. 600/309
5,985,129 A 11/1999 Gough et al. ............... 205/724
5,999,848 A 12/1999 Gord et al. ...................... 607/2
6,001,067 A 12/1999 Shults et al. ................ 600/584
6,001,471 A 12/1999 Bries et al.
6,011,984 A 1/2000 Van Antwerp et al.
6,013,113 A 1/2000 Mika
6,016,448 A 1/2000 Busacker et al. .............. 607/29
6,049,727 A 4/2000 Crothall
6,059,946 A 5/2000 Yukawa et al.
6,060,640 A 5/2000 Pauley et al.
6,063,637 A 5/2000 Arnold et al.
6,066,083 A 5/2000 Slater et al.
6,081,736 A 6/2000 Colvin et al. ............... 600/377
6,083,710 A 7/2000 Heller et al. ................ 600/347
6,088,608 A 7/2000 Schulman et al. ........... 600/345
6,091,975 A 7/2000 Daddona et al.
6,093,172 A 7/2000 Funderburk et al.
6,103,033 A 8/2000 Say et al.
6,115,634 A 9/2000 Donders et al.
6,119,028 A 9/2000 Schulman et al. ........... 600/345
6,121,009 A 9/2000 Heller et al.
6,122,536 A 9/2000 Sun et al.
6,134,461 A 10/2000 Say et al.
6,135,978 A 10/2000 Houben et al. ................ 604/66
6,144,869 A 11/2000 Berner et al. ............... 600/347
6,144,871 A 11/2000 Saito et al.
6,162,611 A 12/2000 Heller et al. .................. 435/14
6,167,614 B1 1/2001 Tuttle et al.
6,175,752 B1 1/2001 Say et al. .................... 600/345
6,180,416 B1 1/2001 Kurnik et al.
6,187,062 B1 2/2001 Oweis et al.
6,189,536 B1 2/2001 Martinez et al.
6,200,772 B1 3/2001 Vadgama et al. .............. 435/25
6,201,980 B1 3/2001 Darrow et al. .............. 600/347
6,206,856 B1 3/2001 Mahurkar
6,208,894 B1 3/2001 Schulman et al. .............. 607/2
6,212,416 B1 4/2001 Ward et al. .................. 600/345
6,214,185 B1 4/2001 Offenbacher et al.
6,223,080 B1 4/2001 Thompson
6,223,083 B1 4/2001 Rosar
6,230,059 B1 5/2001 Duffin ......................... 607/60
6,231,879 B1 5/2001 Li et al. ...................... 424/422
6,233,471 B1 5/2001 Berner et al. ............... 600/345
6,241,863 B1 6/2001 Monbouquette ......... 205/777.5
6,248,067 B1 6/2001 Causey, III et al. .......... 600/365
6,254,586 B1 7/2001 Mann et al.
6,256,522 B1 7/2001 Schultz ....................... 600/317
6,259,937 B1 7/2001 Schulman et al. ........... 600/345
6,268,161 B1 7/2001 Han et al.
6,272,364 B1 8/2001 Kurnik
6,272,382 B1 8/2001 Faltys et al.
6,274,285 B1 8/2001 Gries et al. ................. 430/162
6,275,717 B1 8/2001 Gross et al.
6,284,478 B1 9/2001 Heller et al. .................. 435/14
6,285,897 B1 9/2001 Kilcoyne et al.
6,293,925 B1 9/2001 Safabash et al.
6,296,615 B1 10/2001 Brockway et al.
6,299,578 B1 10/2001 Kurnik et al. ............... 600/309
6,300,002 B1 10/2001 Webb et al.
6,309,351 B1 10/2001 Kurnik et al. ............... 600/309
6,309,384 B1 10/2001 Harrington et al. ............ 606/28
6,325,978 B1 12/2001 Labuda et al. ................. 422/84
6,325,979 B1 12/2001 Hahn et al.
6,326,160 B1 12/2001 Dunn et al.
6,329,161 B1 12/2001 Heller et al. .................. 435/14
6,330,464 B1 12/2001 Colvin et al.
6,343,225 B1 1/2002 Clark, Jr.
6,365,670 B1 4/2002 Fry ............................ 24/862
6,366,794 B1 4/2002 Moussy et al.
6,368,274 B1 4/2002 Van Antwerp et al.
6,372,244 B1 4/2002 Antanavich et al. ......... 424/423
6,400,974 B1 6/2002 Lesho

| | | | |
|---|---|---|---|
| 6,405,066 | B1 | 6/2002 | Essenpreis et al. |
| 6,406,066 | B1 | 6/2002 | Uegane |
| 6,409,674 | B1 | 6/2002 | Brockway et al. |
| 6,413,393 | B1 | 7/2002 | Van Antwerp et al. |
| 6,424,847 | B1 | 7/2002 | Mastrototaro et al. |
| 6,442,413 | B1 | 8/2002 | Silver |
| 6,447,448 | B1 | 9/2002 | Ishikawa et al. |
| 6,447,542 | B1 | 9/2002 | Weadock |
| 6,454,710 | B1 | 9/2002 | Ballerstadt et al. |
| 6,459,917 | B1 | 10/2002 | Gowda et al. |
| 6,461,496 | B1 | 10/2002 | Feldman et al. |
| 6,466,810 | B1 | 10/2002 | Ward et al. |
| 6,471,689 | B1 | 10/2002 | Joseph et al. |
| 6,475,750 | B1 | 11/2002 | Han et al. |
| 6,477,392 | B1 | 11/2002 | Honigs et al. |
| 6,477,395 | B2 | 11/2002 | Schulman et al. |
| 6,481,440 | B2 | 11/2002 | Gielen et al. |
| 6,484,046 | B1 | 11/2002 | Say et al. |
| 6,497,729 | B1 | 12/2002 | Moussy et al. |
| 6,498,043 | B1 | 12/2002 | Schulman et al. |
| 6,514,718 | B2 | 2/2003 | Heller et al. .................. 435/14 |
| 6,520,997 | B1 | 2/2003 | Pekkarinen et al. |
| 6,527,729 | B1 | 3/2003 | Turcott |
| 6,528,584 | B2 * | 3/2003 | Kennedy et al. ............ 525/101 |
| 6,537,318 | B1 | 3/2003 | Ita et al. |
| 6,541,107 | B1 | 4/2003 | King et al. ............... 428/312.6 |
| 6,545,085 | B2 | 4/2003 | Kilgour et al. |
| 6,546,268 | B1 | 4/2003 | Ishikawa et al. |
| 6,547,839 | B2 | 4/2003 | Zhang et al. |
| 6,551,496 | B1 | 4/2003 | Moles et al. |
| 6,558,321 | B1 | 5/2003 | Burd et al. |
| 6,560,471 | B1 | 5/2003 | Heller et al. |
| 6,569,521 | B1 | 5/2003 | Sheridan et al. |
| 6,579,498 | B1 | 6/2003 | Eglise |
| 6,585,763 | B1 | 7/2003 | Keilman et al. |
| 6,587,705 | B1 | 7/2003 | Kim et al. |
| 6,607,509 | B2 | 8/2003 | Bobroff et al. |
| 6,613,379 | B2 | 9/2003 | Ward et al. |
| 6,615,078 | B1 | 9/2003 | Burson et al. |
| 6,618,934 | B1 | 9/2003 | Feldman et al. |
| 6,642,015 | B2 | 11/2003 | Vachon et al. |
| 6,645,181 | B1 | 11/2003 | Lavi et al. |
| 6,648,821 | B2 | 11/2003 | Lebel et al. |
| 6,654,625 | B1 | 11/2003 | Say et al. |
| 6,683,535 | B1 | 1/2004 | Utke |
| 6,694,191 | B2 | 2/2004 | Starkweather et al. |
| 6,695,860 | B1 | 2/2004 | Ward et al. |
| 6,699,218 | B2 | 3/2004 | Flaherty et al. |
| 6,702,857 | B2 | 3/2004 | Brauker et al. |
| 6,721,587 | B2 | 4/2004 | Gough |
| 6,731,976 | B2 | 5/2004 | Penn et al. |
| 6,740,075 | B2 | 5/2004 | Lebel et al. |
| 6,741,877 | B1 | 5/2004 | Shults et al. |
| 6,773,565 | B2 | 8/2004 | Ono et al. |
| 6,793,632 | B2 | 9/2004 | Sohrab |
| 6,793,802 | B2 | 9/2004 | Lee et al. |
| 6,804,544 | B2 | 10/2004 | Van Antwerp et al. |
| 6,810,290 | B2 | 10/2004 | Lebel et al. |
| 6,862,465 | B2 | 3/2005 | Shults et al. |
| 6,931,327 | B2 | 8/2005 | Goode et al. |
| 7,074,307 | B2 | 7/2006 | Simpson et al. |
| 7,108,778 | B2 | 9/2006 | Simpson et al. |
| 7,110,803 | B2 | 9/2006 | Shults et al. |
| 7,134,999 | B2 | 11/2006 | Brauker et al. |
| 7,136,689 | B2 | 11/2006 | Shults et al. |
| 7,192,450 | B2 | 3/2007 | Brauker et al. |
| 2002/0022883 | A1 | 2/2002 | Burg |
| 2002/0042090 | A1 | 4/2002 | Heller et al. |
| 2002/0151796 | A1 | 10/2002 | Koulik |
| 2002/0182241 | A1 | 12/2002 | Borenstein et al. |
| 2002/0188185 | A1 | 12/2002 | Sohrab |
| 2002/0193885 | A1 | 12/2002 | Legeay et al. |
| 2003/0006669 | A1 | 1/2003 | Pei et al. |
| 2003/0023317 | A1 | 1/2003 | Brauker et al. |
| 2003/0032874 | A1 | 2/2003 | Rhodes et al. |
| 2003/0036803 | A1 | 2/2003 | McGhan et al. |
| 2003/0059631 | A1 * | 3/2003 | Al-Lamee .................. 428/448 |
| 2003/0070548 | A1 | 4/2003 | Clausen |
| 2003/0076082 | A1 | 4/2003 | Morgan et al. |
| 2003/0078481 | A1 | 4/2003 | McIvor et al. |
| 2003/0078560 | A1 | 4/2003 | Miller et al. |
| 2003/0091433 | A1 | 5/2003 | Tam et al. |
| 2003/0125613 | A1 | 7/2003 | Enegren et al. |
| 2003/0188427 | A1 | 10/2003 | Say et al. |
| 2003/0199744 | A1 | 10/2003 | Buse et al. |
| 2003/0217966 | A1 | 11/2003 | Tapsak et al. |
| 2003/0235817 | A1 | 12/2003 | Bartkowiak et al. |
| 2004/0008761 | A1 | 1/2004 | Kelliher et al. |
| 2004/0010207 | A1 | 1/2004 | Flaherty et al. |
| 2004/0011671 | A1 | 1/2004 | Shults et al. |
| 2004/0015134 | A1 | 1/2004 | Lavi et al. |
| 2004/0030285 | A1 | 2/2004 | Lavi et al. |
| 2004/0030294 | A1 | 2/2004 | Mahurkar |
| 2004/0039406 | A1 | 2/2004 | Jessen |
| 2004/0045879 | A1 | 3/2004 | Shults et al. |
| 2004/0068230 | A1 | 4/2004 | Estes et al. |
| 2004/0106857 | A1 | 6/2004 | Gough |
| 2004/0186362 | A1 | 9/2004 | Brauker et al. |
| 2004/0186365 | A1 | 9/2004 | Jin et al. |
| 2004/0199059 | A1 | 10/2004 | Brauker et al. |
| 2004/0219664 | A1 | 11/2004 | Heller et al. |
| 2005/0027180 | A1 | 2/2005 | Goode et al. |
| 2005/0027181 | A1 | 2/2005 | Goode et al. |
| 2005/0027463 | A1 | 2/2005 | Goode et al. |
| 2005/0031689 | A1 | 2/2005 | Shults et al. |
| 2005/0033132 | A1 | 2/2005 | Shults et al. |
| 2005/0043598 | A1 | 2/2005 | Goode et al. |
| 2005/0051427 | A1 | 3/2005 | Brauker et al. |
| 2005/0054909 | A1 | 3/2005 | Petisce et al. |
| 2005/0056552 | A1 | 3/2005 | Simpson et al. |
| 2005/0090607 | A1 | 4/2005 | Tapsak et al. |
| 2005/0192557 | A1 | 9/2005 | Brauker et al. |
| 2005/0242479 | A1 | 11/2005 | Petisce et al. |
| 2005/0245795 | A1 | 11/2005 | Goode et al. |
| 2005/0245799 | A1 | 11/2005 | Brauker et al. |
| 2006/0015020 | A1 | 1/2006 | Neale et al. |
| 2007/0032718 | A1 | 2/2007 | Shults et al. |

FOREIGN PATENT DOCUMENTS

| | | |
|---|---|---|
| EP | 0107634 | 5/1984 |
| EP | 0 127 958 | 12/1984 |
| EP | 0 320 109 | 6/1989 |
| EP | 0 353 328 | 2/1990 |
| EP | 0 390 390 | 10/1990 |
| EP | 0 534 074 | 3/1993 |
| EP | 0535898 | 4/1993 |
| EP | 776628 A2 | 6/1997 |
| EP | 0885932 | 12/1998 |
| EP | 0817809 | 7/2002 |
| FR | 2 656 423 | 6/1991 |
| FR | 2760962 | 9/1998 |
| GB | 1442303 | 7/1976 |
| GB | 2149918 | 6/1985 |
| JP | 62083849 | 4/1987 |
| WO | WO 89/02720 | 4/1989 |
| WO | WO 90/00738 | 1/1990 |
| WO | WO 92/07525 | 5/1992 |
| WO | WO 92/13271 | 8/1992 |
| WO | WO 93/14693 | 8/1993 |
| WO | WO 93/19701 | 10/1993 |
| WO | WO 94/22367 | 10/1994 |
| WO | WO 95/07109 | 3/1995 |
| WO | WO 96/01611 | 1/1996 |
| WO | WO 96/14026 | 5/1996 |
| WO | WO 96/25089 | 8/1996 |

| | | | |
|---|---|---|---|
| WO | WO 96/30431 | | 10/1996 |
| WO | WO 96/32076 | | 10/1996 |
| WO | WO 96/36296 | | 11/1996 |
| WO | WO 97/01986 | | 1/1997 |
| WO | WO 97/43633 | | 11/1997 |
| WO | WO 98/24358 | | 6/1998 |
| WO | WO 99/56613 | | 4/1999 |
| WO | WO 00/13003 | | 3/2000 |
| WO | WO0019887 | | 4/2000 |
| WO | WO 00/32098 | | 6/2000 |
| WO | WO0033065 | | 6/2000 |
| WO | WO 00/59373 | | 10/2000 |
| WO | WO 00/74753 | | 12/2000 |
| WO | WO 01/12158 | | 2/2001 |
| WO | WO0120019 | | 3/2001 |
| WO | WO0120334 | | 3/2001 |
| WO | WO 01/34243 | A1 | 5/2001 |
| WO | WO 01/43660 | | 6/2001 |
| WO | WO 01/58348 | | 8/2001 |
| WO | WO 01/88524 | | 11/2001 |
| WO | WO 01/88534 | A2 | 11/2001 |
| WO | WO 02/053764 | | 7/2002 |
| WO | WO03101862 | A1 | 12/2003 |

OTHER PUBLICATIONS

Bindra et al. 1991. Design and In Vitro Studies of a Needle-Type Glucose Sensor for Subcutaneous Monitoring. Anal. Chem 63:1692-96.

Brauker, J., Abstract: Neovascularization of Cell Transplantation Devices: Membrane Architecture-Driven an Implanted Tissue-Driven Vascularization. Baxter Healthcare Corp.

Brauker, et al. Jun. 27, 1996. Local Inflammatory Response Around Diffusion Chambers Containing Xenografts Transplantation 61(12):1671-1677.

Direct 30/30® meter (Markwell Medical) (Catalog), date unknown.

DuPont[1] Dimension AR® (Catalog), date unknown.

Fischer et al. 1989. Oxygen Tension at the Subcutaneous Implantation Site of Glucose Sensors. Biomed. Biochem 11/12:965-972.

Lyman D. 1960. Polyurethanes. I. The Solution Polymerization of Diisocyanates with Ethylene Glycol. J. Polymer Sci XLV:45:49.

McKean, et al. Jul. 7, 1988. A Telemetry Instrumentation System for Chronically Implanted Glucose and Oxygen Sensors. Transactions on Biomedical Engineering 35:526-532.

Phillips and Smith. 1988. Bromedical Applications of Polyurethanes: Implications of Failure Mechanisms. J. Biomat. Appl. 3:202-227.

Shichiri, et al. 1986. Telemetry Glucose Monitoring Device with Needle-Type Glucose Sensor: A Useful Tool for Blood Glucose Monitoring in Diabetic Individuals. Diabetes Care, Inc. 9(3):208-301.

Stokes. 1988. Polyether Polyurethanes: Biostable or Not? J. Biomat. Appl. 3:228-259.

Tse and Gough. 1987. Time-Dependent Inactivation of Immobilized Glucose Oxidase and Catalase. Biotechnol. Bioeng. 29:705-713.

Updike et al. 1988. Laboratory Evaluation of New Reusable Blood Glucose Sensor. Diabetes Care 11:801-807.

Updike, et al. 1982. Implanting the glucose enzyme electrode: Problems, progress, and alternative solutions. Diabetes Care 5(3):207-212.

Woodward. 1982. How Fibroblasts and Giant Cells Encapsulate Implants: Considerations in Design of Glucose Sensor. Diabetes Care 5:278-281.

Answers.com. "xenogenic." The American Heritage Stedman's Medical Dictionary. Houghton Mifflin Company, 2002. Answers. com Nov. 7, 2006 http://www.Answers.com/topic/xenogenic.

Loffler, et al. 1995. Separation and determination of traces of ammonia in air by means of chromatomembrane cells. Fresenius J Anal Chem 352:613-614.

Pineda, et al. 1996. Bone regeneration with resorbable polymeric membranes. III. Effect of poly(L-lactide) membrane pore size on the bone healing process in large defects. J. Biomedical Materials Research 31:385-394.

ISR for PCT/US02/23902 filed Jul. 26, 2002.

IPER for PCT/US02/23902 filed Jul. 26, 2002.

Office Action dated Apr. 9, 2003 in U.S. Appl. No. 09/916,386.

Office Action dated Dec. 7, 1998 in U.S. Appl. No. 08/811,473.

Office Action dated Jul. 17, 2007 in U.S. Appl. No. 09/447,227.

Office Action dated Mar. 9, 2007 in U.S. Appl. No. 09/447,227.

Office Action dated Aug. 1, 2006 in U.S. Appl. No. 09/447,227.

Office Action dated Apr. 4, 2006 in U.S. Appl. No. 09/447,227.

Office Action dated Sep. 22, 2005 in U.S. Appl. No. 09/447,227.

Office Action dated Nov. 28, 2003 in U.S. Appl. No. 09/447,227.

Office Action dated Jul. 9, 2003 in U.S. Appl. No. 09/447,227.

Office Action dated Jan. 16, 2003 in U.S. Appl. No. 09/447,227.

Office Action dated Jul. 15, 2002 in U.S. Appl. No. 09/447,227.

Office Action dated Jan. 17, 2002 in U.S. Appl. No. 09/447,227.

Office Action dated Aug. 15, 2001 in U.S. Appl. No. 09/447,227.

Office Action dated Aug. 14, 2001 in U.S. Appl. No. 09/489,588.

Office Action dated Feb. 27, 2002 in U.S. Appl. No. 09/489,588.

Office Action dated Jun. 12, 2003 in U.S. Appl. No. 09/489,588.

Office Action dated Sep. 21, 2004 in U.S. Appl. No. 10/657,843.

Office Action dated Sep. 21, 2004 in U.S. Appl. No. 09/916,858.

Office Action dated Mar. 22, 2004 in U.S. Appl. No. 09/916,858.

Office Action dated Aug. 14, 2006 in U.S. Appl. No. 11/039,269.

Office Action dated Feb. 24, 2006 in U.S. Appl. No. 11/039,269.

Office Action dated Nov. 2, 2005 in U.S. Appl. No. 11/039,269.

Office Action dated May 4, 2005 in U.S. Appl. No. 11/039,269.

Office Action dated Feb. 24, 2006 in U.S. Appl. No. 10/646,333.

Office Action dated Jun. 6, 2003 in U.S. Appl. No. 10/646,333.

Office Action dated Sep. 22, 2004 in U.S. Appl. No. 10/646,333.

Office Action dated Oct. 16, 2006 in U.S. Appl. No. 10/647,065.

Office Action dated May 23, 2007 in U.S. Appl. No. 11/055,779.

Office Action dated Sep. 21, 2007 in U.S. Appl. No. 10/838,912.

Atanasov, et al. Biosensor for Continuous Glucose Monitoring. Biotechnology and Bioengineering 1994, 43, 262-266.

Baker, et al. Dynamic concentration challenges for biosensor characterization. Biosens Bioelectron 1993, 8, 433-441.

Bani Amer, M. M. An accurate amperometric glucose sensor based glucometer with eliminated cross-sensitivity. J Med Eng Technol 2002, 26, 208-13.

Beach, et al. Subminiature implantable potentiostat and modified commercial telemetry device for remote glucose monitoring. IEEE Transactions on Instrumentation and Measurement 1999, 48, 1239-1245.

Bindra, et al. Pulsed amperometric detection of glucose in biological fluids at a surface-modified gold electrode. Anal Chem 1989, 61, 2566-2570.

Bode, B. W. Clinical utility of the continuous glucose monitoring system. Diabetes Technol Ther 2000, 2 Suppl 1, S35-41.

Bode, et al. Continuous glucose monitoring used to adjust diabetes therapy improves glycosylated hemoglobin: a pilot study. Diabetes Res Clin Pract 1999, 46, 183-190.

Bode, et al. Using the continuous glucose monitoring system to improve the management of type 1 diabetes. Diabetes Technol Ther 2000, 2 Suppl 1, S43-8.

Bott, A. W. A Comparison of Cyclic Voltammetryand Cyclic Staircase Voltammetry. Current Separations 1997, 16:1, 23-26.

Brauker, et al. Neovascularization of synthetic membranes directed by membrane microarchitecture. J Biomed Mater Res 1995, 29, 1517-1524.

Brauker, et al. Sustained expression of high levels of human factor IX from human cells implanted within an immunoisolation device into athymic rodents. Hum Gene Ther 1998, 9, 879-888.

Brauker, J.H. Unraveling Mysteries at the Biointerface: Molecular Mediator of Inhibition of Blood Vessel Formation in the Foreign Body Capsule Revealed. Surfacts Biomaterials 2001,6, 1;5.

Bremer, et al. Benchmark data from the literature for evaluation of new glucose sensing technologies. Diabetes Technol Ther 2001, 3, 409-418.

Brunner, et al. Validation of home blood glucose meters with respect to clinical and analytical approaches. Diabetes Care 1998, 21, 585-590.

D'Arrigo, et al. Porous-Si based bioreactors for glucose monitoring and drugs production. Proc. of SPIE 2003, 4982, 178-184.

Dixon, et al. Characterization in vitro and in vivo of the oxygen dependence of an enzyme/polymer biosensor for monitoring brain glucose. J Neurosci Methods 2002, 119, 135-142.
Ernst, et al. Reliable glucose monitoring through the use of microsystem technology. Anal Bioanal Chem 2002, 373, 758-761.
Fare, et al. Functional characterization of a conducting polymer-based immunoassay system. Biosens Bioelectron 1998, 13, 459-470.
Frost, et al. Implantable chemical sensors for real-time clinical monitoring: progress and challenges. Curr Opin Chem Biol 2002, 6, 633-641.
Geller, et al. Use of an immunoisolation device for cell transplantation and tumor immunotherapy. Ann NY Acad Sci 1997, 831, 438-451.
Gerritsen, M. Problems associated with subcutaneously implanted glucose sensors. Diabetes Care 2000, 23, 143-5.
Gerritsen, et al. Influence of inflammatory cells and serum on the performance of implantable glucose sensors. J Biomed Mater Res 2001, 54, 69-75.
Gerritsen, et al. Performance of subcutaneously implanted glucose sensors for continuous monitoring. Neth J Med 1999, 54, 167-179.
Gilligan et al. Evaluation of a subcutaneous glucose sensor out to 3 months in a dog model. Diabetes Care 1994, 17:8, 882-887.
Gough, et al. Immobilized glucose oxidase in implantable glucose sensor technology. Diabetes Technol Ther 2000, 2, 377-380.
Gross, et al. Performance evaluation of the MiniMed continuous glucose monitoring system during patient home use. Diabetes Technol Ther 2000, 2, 49-56.
Gross, Todd, "Letters to the Editor Re: Diabetes Technology & Therapeutics, 2000;2:49-56," vol. 3, No. 1, p. 130-131, 2001.
Gross, et al. Efficacy and reliability of the continuous glucose monitoring system. Diabetes Technol Ther 2000, 2 Suppl 1, S19-26.
Hall, et al. Electrochemical oxidation of hydrogen peroxide at platinum electrodes. Part 1. An adsorption-controlled mechanism. Electrochimica Acta 1998, 43, 579-588.
Hall, et al. Electrochemical oxidation of hydrogen peroxide at platinum electrodes. Part II: effect of potential. Electrochimica Acta 1998, 43, 2015-2024.
Hall, et al. Electrochemical oxidation of hydrogen peroxide at platinum electrodes. Part III: Effect of temperature. Electrochimica Acta 1999, 44, 2455-2462.
Hall, et al. Electrochemical oxidation of hydrogen peroxide at platinum electrodes. Part IV: phosphate buffer dependence. Electrochimica Acta 1999, 44, 4573-4582.
Hall, et al. Electrochemical oxidation of hydrogen peroxide at platinum electrodes. Part V: inhibition by chloride. Electrochimica Acta 2000, 45, 3573-3579.
Hitchman, M. Measurement of Dissolved Oxygen. Chemical Analysis 1978, 49, 34-123.
Huang, C., O'Grady, W.E.; Yeager, E. Electrochemical Generation of Oxygen. 1: The Effects of Anions and Cations on Hydrogen Chemisorption and Aniodic Oxide Film Formation on Platinum Electrode. 2: The Effects of Anions and Cations on Oxygen Generation on Platinum Electrode, pp. 1-116, Aug. 1975.
lshikawa, et al. Initial evaluation of a 290-microm diameter subcutaneous glucose sensor: glucose monitoring with a biocompatible, flexible-wire, enzyme-based amperometric microsensor in diabetic and nondiabetic humans. J Diabetes Complications 1998, 12, 295-301.
Jensen, et al. Fast Wave Forms for Pulsed Electrochemical Detection of Glucose by Incorporation of Reduction Desorption of Oxidation Products. Analytical Chemistry 1997, 69, 1776-1781.
Johnson, et al. In vivo evaluation of an electroenzymatic glucose sensor implanted in subcutaneous tissue. Biosens Bioelectron 1992, 7, 709-714.
Jovanovic, L. The role of continuous glucose monitoring in gestational diabetes mellitus. Diabetes Technol Ther 2000, 2 Suppl 1, S67-71.
Kargol, et al. Studies on the structural properties of porous membranes: measurement of linear dimensions of solutes. Biophys Chem 2001, 91, 263-271.
Kaufman, F. R. Role of the continuous glucose monitoring system in pediatric patients. Diabetes Technol Ther 2000, 2 Suppl 1, S49-52.
Kiechle, F.L. The impact of continuous glucose monitoring on hospital point-of-care testing programs. Diabetes Technol Ther 2001, 3, 647-649.
Koschinsky, et al. Sensors for glucose monitoring: technical and clinical aspects. Diabetes Metab Res Rev 2001, 17, 113-123.
Kruger, et al. Psychological motivation and patient education: a role for continuous glucose monitoring. Diabetes Technol Ther 2000, 2 Suppl 1, S93-7.
Lee, et al. Effects of pore size, void volume, and pore connectivity on tissue responses. Society for Biomaterials 1999, $25^{th}$ Annual Meeting, 171.
Lerner, et al. An implantable electrochemical glucose sensor. Ann N Y Acad Sci 1984, 428, 263-278.
Leypoldt, et al. Model of a two-substrate enzyme electrode for glucose. Anal Chem 1984, 56, 2896-2904.
Makale, et al. Tissue window chamber system for validation of implanted oxygen sensors. Am J Physiol Heart Circ Physiol 2003, 284, 1-24.
Malin, et al. Noninvasive Prediction of Glucose by Near-Infrared Diffuse Reflectance Spectroscopy. Clinical Chemistry, 45:9, 1651-1658, 1999.
Maran, et al. Continuous subcutaneous glucose monitoring in diabetic patients: a multicenter analysis. Diabetes Care 2002, 25, 347-52.
Mastrototaro, J. J.; Gross, T. M., Reproducibility of the continuous glucose monitoring system matches previous reports and the intended use of the product. *Diabetes Care*, 26:256; author reply p. 257, 2003.
Matsumoto, et al. A long-term lifetime amperometric glucose sensor with a perfluorocarbon polymer coating. Biosens Bioelectron 2001, 16, 271-276.
Miller, A. Human monocyte/macrophage activation and interleukin 1 generation by biomedical polymers. J Biomed Mater Res 1988, 23, 713-731.
Miller, et al. Generation of IL-1 like activity in response to biomedical polymer implants: a comparison of in vitro and in vivo models. J Biomed Mater Res 1989, 23, 1007-1026.
Miller, et al. In vitro stimulation of fibroblast activity by factors generated from human monocytes activated by biomedical polymers. Journal of J Biomed Mater Res 1989, 23, 911-930.
Moussy, et al. Biomaterials community examines biosensor biocompatibility. Diabetes Technol Ther 2000, 2, 473-477.
Mowery, et al. Preparation and characterization of hydrophobic polymeric films that are thromboresistant via nitric oxide release. Biomaterials 2000, 21, 9-21.
Myler, et al. Ultra-thin-polysiloxane-film-composite membranes for the optimisation of amperometric oxidase enzyme electrodes. Biosens Bioelectron 2002, 17, 35-43.
Nam, et al. A novel fabrication method of macroporous biodegradable polymer scaffolds using gas foaming salt as a porogen additive. J Biomed Mater Res 2000, 53, 1-7.
Palmisano, et al. Simultaneous monitoring of glucose and lactate by an interference and cross-talk free dual electrode amperometric biosensor based on electropolymerized thin films. Biosens Bioelectron 2000, 15, 531-539.
Pitzer, et al. Detection of hypoglycemia with the GlucoWatch biographer. Diabetes Care 2001, 24, 881-5.
Poitout, et al. A glucose monitoring system for on line estimation in man of blood glucose concentration using a miniaturized glucose sensor implanted in the subcutaneous tissue and a wearable control unit. Diabetologia 1993, 36, 658-663.
Postlethwaite, et al. Interdigitated Array Electrode as an Alternative to the Rotated Ring-Disk Electrode for Determination of the Reaction Products of Dioxygen Reduction. Analytical Chemistry 1996, 68, 2951-2958.
Ratner, B.D. Reducing capsular thickness and enhancing angiogenesis around implant drug release systems. J Control Release 2002, 78, 211-218.
Reach, Gerard, "Letters to the Editor Re: Diabetes Technology & Therapeutics, 2000;2:49-56," vol. 3, No. 1, p. 129-130, 2001.

Rhodes et al., Prediction of pocket-portable and implantable glucose enzyme electrode performance from combined species permeability and digital simulation analysis. Analytical Chemistry 1994, 66, 1520-1529.
Sansen, et al. A smart sensor for the voltammetric measurement of oxygen or glucose concentrations. Sensors and Actuators 1990, 1, 298-302.
Sansen, et al. "Glucose sensor with telemetry system." Ko, W.H. (Ed). Implantable Sensors for Closed Loop Prosthetic Systems, Ch. 12, 167-175, Futura Publishing Co. (1985).
Schmidt, et al. Glucose concentration in subcutaneous extracellular space. Diabetes Care 1993, 16, 695-700.
Schoemaker, et al. The SCGM1 System: Subcutaneous Continuous Glucose Monitoring Based on Microdialysis Technique. Diabetes Technol Ther 2003, 5, 599-608.
Shults, et al. A telemetry-instrumentation system for monitoring multiple subcutaneously implanted glucose sensors. IEEE Transactions on Biomedical Engineering 1994, 41, 937-942.
Sieminski, et al. Biomaterial-microvasculature interactions. Biomaterials 2000, 21, 2233-2241.
Skyler, J. S. The economic burden of diabetes and the benefits of improved glycemic control: the potential role of a continuous glucose monitoring system. Diabetes Technol Ther 2000, 2 Suppl 1, S7-12.
Steil, et al. Determination of plasma glucose during rapid glucose excursions with a subcutaneous glucose sensor. Diabetes Technol Ther 2003, 5, 27-31.
Tanenberg, et al. Continuous glucose monitoring system: a new approach to the diagnosis of diabetic gastroparesis. Diabetes Technol Ther 2000, 2 Suppl 1, S73-80.
Tang, et al. Fibrin(ogen) mediates acute inflammatory responses to biomaterials. J Exp Med 1993, 178, 2147-2156.
Tang, et al. Inflammatory responses to biomaterials. Am J Clin Pathol 1995, 103, 466-471.
Tang, et al. Mast cells mediate acute inflammatory responses to implanted biomaterials. Proc Natl Acad Sci U S A 1998, 95, 8841-8846.
Tang, et al. Molecular determinants of acute inflammatory responses to biomaterials. J Clin Invest 1996, 97, 1329-1334.
Thome-Duret, et. al. Modification of the sensitivity of glucose sensor implanted into subcutaneous tissue. Diabetes Metab 1996, 22, 174-178.
Tibell, et al. Survival of macroencapsulated allogeneic parathyroid tissue one year after transplantation in nonimmunosuppressed humans. Cell Transplant 2001, 10, 591-9.
Tierney, et al. The GlucoWatch biographer: a frequent automatic and noninvasive glucose monitor. Ann Med 2000, 32, 632-641.
Updike et al. Enzymatic glucose sensors: improved long-term performance in vitro and in vivo. ASAIO Journal 1994, 40, 157-163.
Updike et al. "Principles of long-term fully implanted sensors with emphasis on radiotelemetric monitoring of blood glucose from inside a subcutaneous foreign body capsule (FBC)." Fraser, D.M. (Ed.). *Biosensors in the body: continuous in vivo monitoring*, Chap. 4, pp. 117-137, John Wiley & Sons Ltd., (1997).
Updike, et al. A subcutaneous glucose sensor with improved longevity, dynamic range, and stability of calibration. Diabetes Care 2000, 23, 208-214.
Updike, et al. The enzyme electrode. Nature 1967, 214, 986-988.
Wagner, et al. A. Continuous amperometric monitoring of glucose in a brittle diabetic chimpanzee with a miniature subcutaneous electrode. Proc Natl Acad Sci U S A 1998, 95, 6379-6382.
Ward et al. A new amperometric glucose microsensor: in vitro and short-term in vivo evaluation. Biosensors & Bioelectronics 2002, 17,181-189.
Ward, et al., Rise in background current over time in a subcutaneous glucose sensor in the rabbit: relevance to calibration and accuracy. Biosensors & Bioelectronics 2000, 15, 53-61.
Wilkins, E.; Atanasov, P.; Muggenburg, B. A., "Integrated implantable device for long-term glucose monitoring," Biosens Bioelectron 1995, 10, 485-494.
Wilson, et al. Enzyme-based biosensors for in vivo measurements. Chem Rev 2000, 100:2693-2704.
Wu, et al. In situ electrochemical oxygen generation with an immunoisolation device. Ann N Y Acad Sci 1999, 875, 105-125.
Yang, et al. Development of needle-type glucose sensor with high selectivity. Science and Actuators B 1998, 46, 249-256.
U.S. Appl. No. 09/447,227, filed Nov. 22, 1999.
U.S. Appl. No. 10/632,537, filed Aug. 1, 2003.
U.S. Appl. No. 10/633,329, filed Aug. 1, 2003.
U.S. Appl. No. 10/633,367, filed Aug. 1, 2003.
U.S. Appl. No. 10/633,404, filed Aug. 1, 2003.
U.S. Appl. No. 10/646,333, filed Aug. 22, 2003.
U.S. Appl. No. 10/647,065, filed Aug. 22, 2003.
U.S. Appl. No. 10/648,849, filed Aug. 22, 2003.
U.S. Appl. No. 10/695,636, filed Oct. 28, 2003.
U.S. Appl. No. 10/789,359, filed Feb. 26, 2004.
U.S. Appl. No. 10/838,658, filed May 3, 2004.
U.S. Appl. No. 10/838,909, filed May 3, 2004.
U.S. Appl. No. 10/838,912, filed May 3, 2004.
U.S. Appl. No. 10/842,716, filed May 10, 2004.
U.S. Appl. No. 10/846,150, filed May 14, 2004.
U.S. Appl. No. 10/885,476, filed Jul. 6, 2004.
U.S. Appl. No. 10/896,637, filed Jul. 21, 2004.
U.S. Appl. No. 10/897,772, filed Jul. 21, 2004.
U.S. Appl. No. 10/896,639, filed Jul. 21, 2004.
U.S. Appl. No. 10/897,377, filed Jul. 21, 2004.
U.S. Appl. No. 10/896,312, filed Jul. 21, 2004.
Abel, P. U.; von Woedtke, T. Biosensors for in vivo glucose measurement: can we cross the experimental stage. Biosens Bioelectron 2002, 17, 1059-1070.
Atanasov, P.; Yang, S.; Salehi, C.; Ghindilis, A. L.; Wilkins, E.; Schade, D. Implantation of a refillable glucose monitoring-telemetry device. Biosens Bioelectron 1997, 12, 669-680.
Bowman, L.; Meindl, J. D. The packaging of implantable integrated sensors. IEEE Trans Biomed Eng 1986, 33, 248-255.
Cai, Q.; Zeng, K.; Ruan, C.; Desai, T. A.; Grimes, C. A. A wireless, remote query glucose biosensor based on a pH-sensitive polymer. Anal Chem 2004, 76, 4038-4043.
Cox, D. J.; Clarke, W. L.; Gonder-Frederick, L.; Pohl, S.; Hoover, C.; Snyder, A.; Zimbelman, L.; Carter, W. R.; Bobbitt, S.; Pennebaker, J. Accuracy of perceiving blood glucose in IDDM. Diabetes Care 1985, 8, 529-536.
El-Sa'ad, L.; Yates, D. Moisture Absorption by Epoxy Resins: the Reverse Thermal Effect. Journal of Materials Science 1990, 25, 3577-3582.
Feldman, B.; Brazg, R.; Schwartz, S.; Weinstein, R. A continuous glucose sensor based on wired enzyme technology—results from a 3-day trial in patients with type 1 diabetes. Diabetes Technol Ther 2003, 5, 769-779.
Garg, S.; Schwartz, S.; Edelman, S. Improved Glucose Excursions Using an Implantable Real-Time Continuous Glucose Sensor in Adults wtih Type I Diabetes. Diabetes Care 2004, 27, 734-738.
Gilligan, B. C.; Shults, M.; Rhodes, R. K.; Jacobs, P. G.; Brauker, J. H.; Pintar, T. J.; Updike, S. J. Feasibility of continuous long-term glucose monitoring from a subcutaneous glucose sensor in humans. Diabetes Technol Ther 2004, 6, 378-386.
Heller, A. Implanted electrochemical glucose sensors for the management of diabetes. Annu Rev Biomed Eng 1999, 1, 153-175.
Heller, A. Plugging metal connectors into enzymes. Nat Biotechnol 2003, 21, 631-2.
Hrapovic, S.; Luong, J. H. Picoamperometric detection of glucose at ultrasmall platinum-based biosensors: preparation and characterization. Anal Chem 2003, 75, 3308-3315.
Hunter, I., Jones, L., Kanigan, T., Brenan, C., Sanbol, L. Sosnowski, L. Minimally Invasive Glucose Sensor and Insulin Delivery System. MIT Home Automation and Healthcare Consortium 2000.
Jeutter, D. C. A transcutaneous implanted battery recharging and biotelemeter power switching system. IEEE Trans Biomed Eng 1982, 29, 314-321.
Kang, S. K.; Jeong, R. A.; Park, S.; Chung, T. D.; Park, S.; Kim, H. C. In vitro and short-term in vivo characteristics of a Kel-F thin film modified glucose sensor. Anal Sci 2003, 19, 1481-1486.
Kraver, K.; Guthaus, M. R.; Strong, T.; Bird, P.; Cha, G.; Hoeld, W.; Brown, R. A mixed-signal sensor interface microinstrument. Sensors and Actuators A: Physical 2001, 91, 266-277.
March, W. F. Dealing with the delay. Diabetes Technol Ther 2002, 4, 49-50.

Mastrototaro, J. J. The MiniMed continuous glucose monitoring system. Diabetes Technol Ther 2000, 2 Suppl 1, S13-8.
McCartney, L. J.; Pickup, J. C.; Rolinski, O. J.; Birch, D. J. Near-infrared fluorescence lifetime assay for serum glucose based on allophycocyanin-labeled concanavalin A. Anal Biochem 2001, 292, 216-221.
McGrath, M. J.; Iwuoha, E. I.; Diamond, D.; Smyth, M. R. The use of differential measurements with a glucose biosensor for interference compensation during glucose determinations by flow injection analysis. Biosens Bioelectron 1995, 10, 937-943.
Memoli, A.; Annesini, M. C.; Mascini, M.; Papale, S.; Petralito, S. A comparison between different immobilised glucoseoxidase-based electrodes. J Pharm Biomed Anal 2002, 29, 1045-1052.
Moatti-Sirat, D.; Capron, F.; Poitout, V.; Reach, G.; Bindra, D. S.; Zhang, Y.; Wilson, G. S.; Thevenot, D. R. Towards continuous glucose monitoring: in vivo evaluation of a miniaturized glucose sensor implanted for several days in rat subcutaneous tissue. Diabetologia 1992, 35, 224-230.
Ohara, T. J.; Rajagopalan, R.; Heller, A. "Wired" enzyme electrodes for amperometric determination of glucose or lactate in the presence of interfering substances. Anal Chem 1994, 66, 2451-2457.
Okuda, J.; Miwa, I. Mutarotase effect on micro determinations of D-glucose and its anomers with -D-glucose oxidase. Anal Biochem 1971, 43, 312-315.
Patel, H.; Li, X.; Karan, H. I. Amperometric glucose sensors based on ferrocene containing polymeric electron transfer systems-a preliminary report. Biosens Bioelectron 2003; 18, 1073-6.
Pichert, J. W.; Campbell, K.; Cox, D. J.; D'Lugin, J. J.; Moffat, J. W.; Polonsky, W. H.; CN , -. . P. o. G. D. P. S. G. Issues for the coming age of continuous glucose monitoring. Diabetes Educ 2000, 26, 969-980.
Quinn, C. A.; Connor, R. E.; Heller, A. Biocompatible, glucose-permeable hydrogel for in situ coating of implantable biosensors. Biomaterials 1997, 18, 1665-1670.
Reach, G.; Abel, P.; Fischer, U. A Method for Evaluating in vivo the Functional Characteristics of Glucose Sensors. Biosensors 1986, 2, 211-220.
Schuler, R.; Wittkampf, M.; Chemnitius, G. C. Modified gas-permeable silicone rubber membranes for covalent immobilisation of enzymes and their use in biosensor development. Analyst 1999, 124, 1181-1184.
Selam, J. L. Management of diabetes with glucose sensors and implantable insulin pumps. From the dream of the 60s to the realities of the 90s. ASAIO J 1997, 43,137-142.
Service, R. F. Can sensors make a home in the body? Science 2002, 297, 962-3.
Shichiri, M.; Kawamori, R.; Yamasaki, Y.; Hakui, N.; Abe, H. Wearable artificial endocrine pancrease with needle-type glucose sensor. Lancet 1982, 2, 1129-1131.
Shichiri, M.; Kawamori, R.; Yamasaki, Y.; Hakui, N.; Asakawa, N.; Abe, H. Needle-type Glucose Sensor for Wearable Artificial Endocrine Pancreas. Book Implantable Sensors 1985, 197-210.
Sriyudthsak, M.; Cholapranee, T.; Sawadsaringkarn, M.; Yupongchaey, N.; Jaiwang, P. Enzyme-epoxy membrane based glucose analyzing system and medical applications. Biosens Bioelectron 1996, 11, 735-742.
Sternberg, R.; Barrau, M. B.; Gangiotti, L.; Thevenot, D. R.; Bindra, D. S.; Wilson, G. S.; Velho, G.; Froguel, P.; Reach, G. Study and development of multilayer needle-type enzyme-based glucose microsensors. Biosensors 1989, 4, 27-40.
Thome-Duret, V.; Aussedat, B.; Reach, G.; Gangnerau, M. N.; Lemonnier, F.; Klein, J. C.; Zhang, Y.; Hu, Y.; Wilson, G. S. Continuous glucose monitoring in the free-moving rat. Metabolism 1998, 47, 799-803.
Tierney, M. J.; Garg, S.; Ackerman, N. R.; Fermi, S. J.; Kennedy, J.; Lopatin, M.; Potts, R. O.; Tamada, J. A. Effect of acetaminophen on the accuracy of glucose measurements obtained with the GlucoWatch biographer. Diabetes Technol Ther 2000, 2, 199-207.
Trecroci, D. A Glimpse into the Future- Continuous Monitoring of Glucose with a Microfiber. Diabetes Interview 2002, 42-43.
Velho, G.; Froguel, P.; Sternberg, R.; Thevenot, D. R.; Reach, G. In vitro and in vivo stability of electrode potentials in needle-type glucose sensors. Influence of needle material. Diabetes 1989, 38, 164-171.
Wang, J.; Liu, J.; Chen, L.; Lu, F. Highly Selective Membrane-Free, Mediator-Free Glucose Biosensor. Anal. Chem. 1994, 66, 3600-3603.
Wang, X.; Pardue, H. L. Improved ruggedness for membrane-based amperometric sensors using a pulsed amperometric method. Anal Chem 1997, 69, 4482-4489.
Ward, W. K.; Wood, M. D.; Troupe, J. E. Understanding Spontaneous Output Fluctuations of an Amperometric Glucose Sensor: Effect of Inhalation Anesthesia and Use of a Nonenzyme Containing Electrode. ASAIO Journal 2000, 540-546.
Wientjes, K. J. C. Development of a glucose sensor for diabetic patients. 2000.
Wilkins, E.; Atanasov, P. Glucose monitoring: state of the art and future possibilities. Med Eng Phys 1995, 18, 273-288.
Wood, W., et al., Hermetic Sealing with Epoxy. Mechanical Engineering Mar. 1990, 1-3.
Bellucci et al. Jan. 1986. Electrochemical behaviour of graphite-epoxy composite materials (GECM) in aqueous salt solutions, Journal of Applied Electrochemistry, 16(1):15-22.
Bobbioni-Harsch et al. 1993. Lifespan of subcutaneous glucose sensors and their performances during dynamic glycaemia changes in rats, J. Biomed. Eng. 15:457-463.
Brooks et al. "Development of an on-line glucose sensor for fermentation monitoring," Biosensors, 3:45-56 (1987/88).
Cass et al. "Ferrocene-mediated enzyme electrodes for amperometric determination of glucose," Anal. Chem., 36:667-71 (1984).
Davies, et al. 1992. Polymer membranes in clinical sensor applications. I. An overview of membrane function, Biomaterials, 13(14):971-978.
Heller, "Electrical wiring of redox enzymes," *Acc. Chem. Res.*, 23:128-134 (1990).
Heller, A. 1992. Electrical Connection of Enzyme Redox Centers to Electrodes. J. Phys. Chem. 96:3579-3587.
Hicks, 1985. In Situ Monitoring, Clinical Chemistry, 31(12):1931-1935.
Hu, et al. 1993. A needle-type enzyme-based lactate sensor for in vivo monitoring, Analytica Chimica Acta, 281:503-511.
Kawagoe et al. 1991. Enzyme-modified organic conducting salt microelectrode, Anal. Chem. 63:2961-2965.
Kerner et al. "The function of a hydrogen peroxide-detecting electroenzymatic glucose electrode is markedly impaired in human sub-cutaneous tissue and plasma," Biosensors & Bioelectronics, 8:473-482 (1993).
Maidan et al. 1992. Elimination of Electrooxidizable Interferent-Produced Currents in Amperometric Biosensors, Analytical Chemistry, 64:2889-2896.
Mastrototaro et al. "An electroenzymatic glucose sensor fabricated on a flexible substrate," Sensors and Actuators B, 5:139-44 (1991).
Murphy, et al. 1992. Polymer membranes in clinical sensor applications. II. The design and fabrication of permselective hydrogels for electrochemical devices, Biomaterials, 13(14):979-990.
Ohara, et al. Dec. 1993. Glucose electrodes based on cross-linked bis(2,2'-bipyridine)chloroosmium(+/2+) complexed poly(1-vinylimidazole) films, Analytical Chemistry, 65:3512-3517.
Pickup et al. "Implantable glucose sensors: choosing the appropriate sensor strategy," Biosensors, 3:335-346 (1987/88).
Pickup et al. "In vivo molecular sensing in diabetes mellitus: an implantable glucose sensor with direct electron transfer," Diabetologia, 32:213-217 (1989).
Pishko et al. "Amperometric glucose microelectrodes prepared through immobilization of glucose oxidase in redox hydrogels," Anal. Chem., 63:2268-72 (1991).
Poitout, et al. 1991. In Vitro and in Vivo Evaluation in Dogs of a Miniaturized Glucose Sensor, ASAIO Transactions, 37:M298-M300.
Reach et al. 1992. Can continuous glucose monitoring be used for the treatment of diabetes? Analytical Chemistry 64(5):381-386.
Rebrin et al. "Automated feedback control of subcutaneous glucose concentration in diabetic dogs," Diabetologia, 32:573-76 (1989).
Sakakida et al. 1993. Ferrocene-Mediated Needle Type Glucose Sensor Covered with Newly Designed Biocompatible Membran, Sensors and Actuators B 13-14:319-322.

Sharkawy et al. 1996. Engineering the tissue which encapsulates subcutaneous implants. I. Diffusion properties, J Biomed Mater Res, 37:401-412.

Shaw et al. "In vitro testing of a simply constructed, highly stable glucose sensor suitable for implantation in diabetic patients," Biosensors & Bioelectronics, 6:401-406 (1991).

Shichiri et al., 1989. Membrane Design For Extending the Long-Life of an Implantable Glucose Sensor. Diab. Nutr. Metab. 2:309-313.

Thompson et al., In Vivo Probes: Problems and Perspectives, Department of Chemistry, University of Toronto, Canada, pp. 255-261, 1986.

Turner and Pickup, "Diabetes mellitus: biosensors for research and management," *Biosensors*, 1:85-115 (1985).

Updike et al. 1997. Principles of long-term fully implanted sensors with emphasis on radiotelemetric monitoring of blood glucose form inside a subcutaneous foreign body capsule (FBC). In Fraser, ed., Biosensors in the Body. New York. John Wiley & Sons, pp. 117-137.

Velho et al. 1989. Strategies for calibrating a subcutaneous glucose sensor. Biomed Biochim Acta 48(11/12):957-964.

von Woedtke et al. 1989. In situ calibration of implanted electrochemical glucose sensors. Biomed Biochim. Acta 48(11/12):943-952.

Wilson et al. 1992. Progress toward the development of an implantable sensor for glucose. Clin. Chem. 38(9):1613-1617.

Office Action dated Oct. 24, 2007 in U.S. Appl. No. 11/055,779.

Office Action dated Jan. 23, 2008 in U.S. Appl. No. 09/447,227.

Office Action dated Mar. 24, 2008 in U.S. Appl. No. 10/838,912.

Office Action dated Jun. 5, 2008 in U.S. Appl. No. 10/846,150.

Office Action mailed Jun. 5, 2008 in U.S. Appl. No. 10/838,909.

Office Action dated Jun. 12, 2008 in U.S. Appl. No. 09/447,227.

Office Action dated Jul. 16, 2008 in U.S. Appl. No. 10/838,912.

Office Action dated Sep. 18, 2008 in U.S. Appl. No. 11/439,630.

Office Action dated Sep. 29, 2008 in U.S. Appl. No. 12/037,830.

Office Action dated Sep. 29, 2008 in U.S. Appl. No. 12/037,812.

Office Action dated Dec. 1, 2008 in U.S. Appl. No. 11/503,367.

Office Action dated Dec. 9, 2008 in U.S. Appl. No. 10/846,150.

Office Action dated Dec. 11, 2008 in U.S. Appl. No. 09/447,227.

Office Action dated Feb. 23, 2009 in U.S. Appl. No. 11/439,630.

Office Action dated Feb. 26, 2009 in U.S. Appl. No. 12/037,830.

Office Action mailed Mar. 16, 2009 in U.S. Appl. No. 10/838,909.

Office Action dated Apr. 1, 2009 in U.S. Appl. No. 12/037,812.

Office Action dated May 26, 2009 in U.S. Appl. No. 09/447,227.

Fianal Office Action dated Jun. 9, 2009 in U.S. Appl. No. 10/846,150.

Office Action dated Jul. 24, 2009 in U.S. Appl. No. 12/037,812.

* cited by examiner

MEMBRANE FOR USE WITH IMPLANTABLE DEVICES

RELATED APPLICATION

This application is a continuation of application Ser. No. 09/916,386, filed Jul. 27, 2001.

FIELD OF THE INVENTION

The present invention relates generally to biointerface membranes that may be utilized with implantable devices such as devices for the detection of analyte concentrations in a biological sample, cell transplantation devices, drug delivery devices and electrical signal delivering or measuring devices. The present invention further relates to methods for determining analyte levels using implantable devices including these membranes. More particularly, the invention relates to novel biointerface membranes, to sensors and implantable devices including these membranes, and to methods for monitoring glucose levels in a biological fluid sample using an implantable analyte detection device.

BACKGROUND OF THE INVENTION

One of the most heavily investigated analyte sensing devices is an implantable glucose sensor for detecting glucose levels in patients with diabetes. Despite the increasing number of individuals diagnosed with diabetes and recent advances in the field of implantable glucose monitoring devices, currently used devices are unable to provide data safely and reliably for long periods of time (e.g., months or years) [See, e.g., Moatti-Sirat et al., Diabetologia 35:224-30 (1992)]. There are two commonly used types of implantable glucose sensing devices. These types are those which are implanted intravascularly and those implanted in tissue.

With reference to devices that may be implanted in tissue, a disadvantage of these devices has been that they tend to lose their function after the first few days to weeks following implantation. At least one reason for this loss of function has been attributed to the fact that there is no direct contact with circulating blood to deliver sample to the tip of the probe of the implanted device. Because of these limitations, it has previously been difficult to obtain continuous and accurate glucose levels. However, this information is often extremely important to diabetic patients in ascertaining whether immediate corrective action is needed in order to adequately manage their disease.

Some medical devices, including implanted analyte sensors, drug delivery devices and cell transplantation devices require transport of solutes across the device-tissue interface for proper function. These devices generally include a membrane, herein referred to as a cell-impermeable membrane that encases the device or a portion of the device to prevent access by host inflammatory or immune cells to sensitive regions of the device.

A disadvantage of cell-impermeable membranes is that they often stimulate a local inflammatory response, called the foreign body response (FBR) that has long been recognized as limiting the function of implanted devices that require solute transport. Previous efforts to overcome this problem have been aimed at increasing local vascularization at the device-tissue interface with limited success.

The FBR has been well described in the literature and is composed of three main layers, as illustrated in FIG. 1. The innermost FBR layer 40, adjacent to the device, is composed generally of macrophages and foreign body giant cells 41

(herein referred to as the barrier cell layer). These cells form a monolayer 40 of closely opposed cells over the entire surface 48*a* of a smooth or microporous (<1.0 .mu·m) membrane 48. The intermediate FBR layer 42 (herein referred to as the fibrous zone), lying distal to the first layer with respect to the device, is a wide zone (30-100 microns) composed primarily of fibroblasts 43 and fibrous matrix 44. The outermost FBR layer 46 is loose connective granular tissue containing new blood vessels 45 (herein referred to as the vascular zone 46). A consistent feature of the innermost layers 40 and 42 is that they are devoid of blood vessels. This has led to widely supported speculation that poor transport of molecules across the device-tissue interface 47 is due to a lack of vascularization near interface 47 (Scharp et al., World J. Surg. 8:221-229 (1984), Colton and Avgoustiniatos J. Biomech. Eng. 113: 152-170 (1991)).

Patents by Brauker et al. (U.S. Pat. No. 5,741,330), and Butler et al. (U.S. Pat. No. 5,913,998), describe inventions aimed at increasing the number of blood vessels adjacent to the implant membrane (Brauker et al.), and growing within (Butler et al.) the implant membrane at the device-tissue interface. The patent of Shults et al. (U.S. Pat. No. 6,001,067) describes membranes that induce angiogenesis at the device-tissue interface of implanted glucose sensors. FIG. 2 illustrates a situation in which some blood vessels 45 are brought close to an implant membrane 48, but the primary layer 40 of cells adherent to the cell-impermeable membrane blocks glucose. This phenomenon is described in further detail below.

In the examples of Brauker et al. (supra), and Shults et al., bilayer membranes are described that have cell impermeable layers that are porous and adhesive to cells. Cells are able to enter into the interstices of these membranes, and form monolayers on the innermost layer, which is aimed at preventing cell access to the interior of the implanted device (cell impenetrable layers). Because the cell impenetrable layers are porous, cells are able to reach pseudopodia into the interstices of the membrane to adhere to and flatten on the membrane, as shown in FIGS. 1 and 2, thereby blocking transport of molecules across the membrane-tissue interface. The known art purports to increase the local vascularization in order to increase solute availability. However, the present studies show that once the monolayer of cells (barrier cell layer) is established adjacent to the membrane, increasing angiogenesis is not sufficient to increase transport of molecules such as glucose and oxygen across the device-tissue interface.

One mechanism of inhibition of transport of solutes across the device-tissue interface that has not been previously discussed in the literature is the formation of a uniform barrier to analyte transport by cells that form the innermost layer of the foreign body capsule. This layer of cells forms a monolayer with closely opposed cells having tight cell-to-cell junctions. When this barrier cell layer forms, it is not substantially overcome by increased local vascularization. Regardless of the level of local vascularization, the barrier cell layer prevents the passage of molecules that cannot diffuse through the layer. Again, this is illustrated in FIG. 2 where blood vessels 45 lie adjacent to the membrane but glucose transport is significantly reduced due to the impermeable nature of the barrier cell layer 40. For example, both glucose and its phosphorylated form do not readily transit the cell membrane and consequently little glucose reaches the implant membrane through the barrier layer cells.

It has been confirmed by the present inventors through histological examination of explanted sensors that the most likely mechanism for inhibition of molecular transport across the device-tissue interface is the barrier cell layer adjacent to the membrane. There is a strong correlation between desired device function and the lack of formation of a barrier cell layer at the device-tissue interface. In the present studies, devices that were observed histologically to have substantial barrier cell layers were functional only 41% of the time after 12 weeks in vivo. In contrast, devices that did not have significant barrier cell layers were functional 86% of the time after 12 weeks in vivo.

Consequently, there is a need for a membrane that interferes with the formation of a barrier layer and protects the sensitive regions of the device from host inflammatory response.

SUMMARY OF THE INVENTION

The biointerface membranes of the present invention interfere with the formation of a monolayer of cells adjacent to the membrane, henceforth referred to herein as a barrier cell layer, which interferes with the transport of oxygen and glucose across a device-tissue interface.

It is to be understood that various biointerface membrane architectures (e.g., variations of those described below) are contemplated by the present invention and are within the scope thereof.

In one aspect of the present invention, a biointerface membrane for use with an implantable device is provided including; a first domain distal to the implantable device wherein the first domain supports tissue ingrowth and interferes with barrier-cell layer formation and a second domain proximal to the implantable device wherein the second domain is resistant to cellular attachment and is impermeable to cells and cell processes.

In another aspect of the present invention, a biointerface membrane is provided including the properties of: promoting tissue ingrowth into; interfering with barrier cell formation on or within; resisting barrier-cell attachment to; and blocking cell penetration into the membrane.

In yet another aspect, a sensor head for use in an implantable device is provided which includes a biointerface membrane of the present invention.

In other aspects, a sensor for use in an implantable device that measures the concentration of an analyte in a biological fluid is provided including the biointerface membrane of the present invention.

In still another aspect of the present invention, a device for measuring an analyte in a biological fluid is provided, the device including the biointerface membrane of the present invention, a housing which includes electronic circuitry, and at least one sensor as provided above operably connected to the electronic circuitry of the housing.

The present invention further provides a method of monitoring analyte levels including the steps of: providing a host, and an implantable device as provided above; and implanting the device in the host. In one embodiment, the device is implanted subcutaneously.

Further provided by the present invention is a method of measuring analyte in a biological fluid including the steps of: providing i) a host, and ii) a implantable device as provided above capable of accurate continuous analyte sensing; and implanting the device in the host. In one embodiment of the method, the device is implanted subcutaneously.

In still another aspect of the present invention, an implantable drug delivery device is provided including a biointerface membrane as provided above. Preferably the implantable drug delivery device is a pump, a microcapsule or a macrocapsule.

The present invention further provides a device for implantation of cells which includes a biointerface membrane as provided above.

Also encompassed by the present invention is an electrical pulse delivering or measuring device, including a biointerface membrane according to that provided above.

The biointerface membranes, devices including these membranes and methods of use of these membranes provided by the invention allow for long term protection of implanted cells or drugs, as well as continuous information regarding, for example, glucose levels of a host over extended periods of time. Because of these abilities, the biointerface membranes of the present invention can be extremely important in the management of transplant patients, diabetic patients and patients requiring frequent drug treatment.

DEFINITIONS

In order to facilitate an understanding of the present invention, a number of terms are defined below.

The terms "biointerface membrane," and the like refer to a permeable membrane that functions as a device-tissue interface comprised of two or more domains. Preferably, the biointerface membrane is composed of two domains. The first domain supports tissue ingrowth, interferes with barrier cell layer formation and includes an open cell configuration having cavities and a solid portion. The second domain is resistant to cellular attachment and impermeable to cells (e.g., macrophages). The biointerface membrane is made of biostable materials and may be constructed in layers, uniform or non-uniform gradients (i.e. anisotropic), or in a uniform or non-uniform cavity size configuration.

The term "domain" refers to regions of the biointerface membrane that may be layers, uniform or non-uniform gradients (e.g. anisotropic) or provided as portions of the membrane.

The term "barrier cell layer" refers to a cohesive monolayer of closely opposed cells (e.g. macrophages and foreign body giant cells) that may adhere to implanted membranes and interfere with the transport of molecules across the membrane.

The phrase "distal to" refers to the spatial relationship between various elements in comparison to a particular point of reference. For example, some embodiments of a device include a biointerface membrane having an cell disruptive domain and a cell impermeable domain. If the sensor is deemed to be the point of reference and the cell disruptive domain is positioned farther from the sensor, then that domain is distal to the sensor.

The term "proximal to" refers to the spatial relationship between various elements in comparison to a particular point of reference. For example, some embodiments of a device include a biointerface membrane having a cell disruptive domain and a cell impermeable domain. If the sensor is deemed to be the point of reference and the cell impermeable domain is positioned nearer to the sensor, then that domain is proximal to the sensor.

The term "cell processes" and the like refers to pseudopodia of a cell.

The term "solid portions" and the like refer to a material having a structure that may or may not have an open-cell configuration, but in either case prohibits whole cells from traveling through or residing within the material.

The term "substantial number" refers to the number of linear dimensions within a domain (e.g. pores or solid portions) in which greater than 50 percent of all dimensions are of the specified size, preferably greater than 75 percent and, most preferably, greater than 90 percent of the dimensions have the specified size.

The term "co-continuous" and the like refers to a solid portion wherein an unbroken curved line in three dimensions exists between any two points of the solid portion.

The term "biostable" and the like refers to materials that are relatively resistant to degradation by processes that are encountered in vivo.

The term "sensor" refers to the component or region of a device by which an analyte can be quantitated.

The term "analyte" refers to a substance or chemical constituent in a biological fluid (e.g., blood or urine) that is intended to be analyzed. A preferred analyte for measurement by analyte detection devices including the biointerface membranes of the present invention is glucose.

The terms "operably connected," "operably linked," and the like refer to one or more components being linked to another component(s) in a manner that allows transmission of signals between the components. For example, one or more electrodes may be used to detect the amount of analyte in a sample and convert that information into a signal; the signal may then be transmitted to an electronic circuit means. In this case, the electrode is "operably linked" to the electronic circuitry.

The term "electronic circuitry" refers to the components of a device required to process biological information obtained from a host. In the case of an analyte measuring device, the biological information is obtained by a sensor regarding a particular analyte in a biological fluid, thereby providing data regarding the amount of that analyte in the fluid. U.S. Pat. Nos. 4,757,022, 5,497,772 and 4,787,398 describe suitable electronic circuit means that may be utilized with devices including the biointerface membrane of the present invention.

The phrase "member for determining the amount of glucose in a biological sample" refers broadly to any mechanism (e.g., enzymatic or non-enzymatic) by which glucose can be quantitated. For example, some embodiments of the present invention utilize a membrane that contains glucose oxidase that catalyzes the conversion of oxygen and glucose to hydrogen peroxide and gluconate: Glucose+O.sub.2=Gluconate+H.sub.2O.sub.2-. Because for each glucose molecule metabolized, there is a proportional change in the co-reactant O.sub.2 and the product H.sub.2O.sub.2, one can monitor the current change in either the co-reactant or the product to determine glucose concentration.

The term "host" refers generally to mammals, particularly humans.

The term "accurately" means, for example, 90% of measured glucose values are within the "A" and "B" region of a standard Clarke error grid when the sensor measurements are compared to a standard reference measurement. It is understood that like any analytical device, calibration, calibration validation and recalibration are required for the most accurate operation of the device.

The phrase "continuous glucose sensing" refers to the period in which monitoring of plasma glucose concentration is continuously performed, for example, about every 10 minutes.

DETAILED DESCRIPTION OF THE PREFERRED EMBODIMENT

Figure 1:
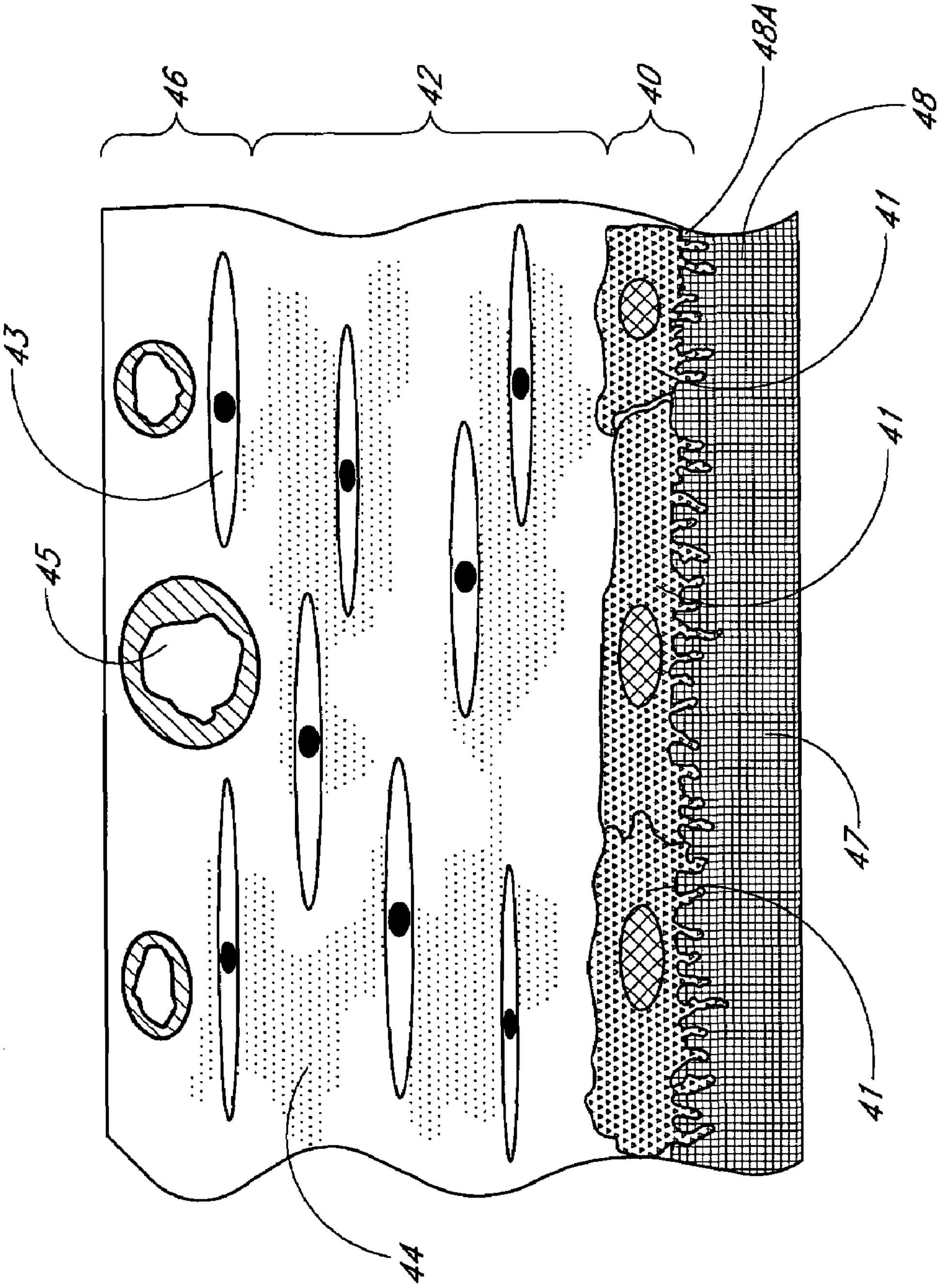
FIG. 1 is an illustration of classical three-layered foreign body response to a synthetic membrane implanted under the skin.
Figure 2:
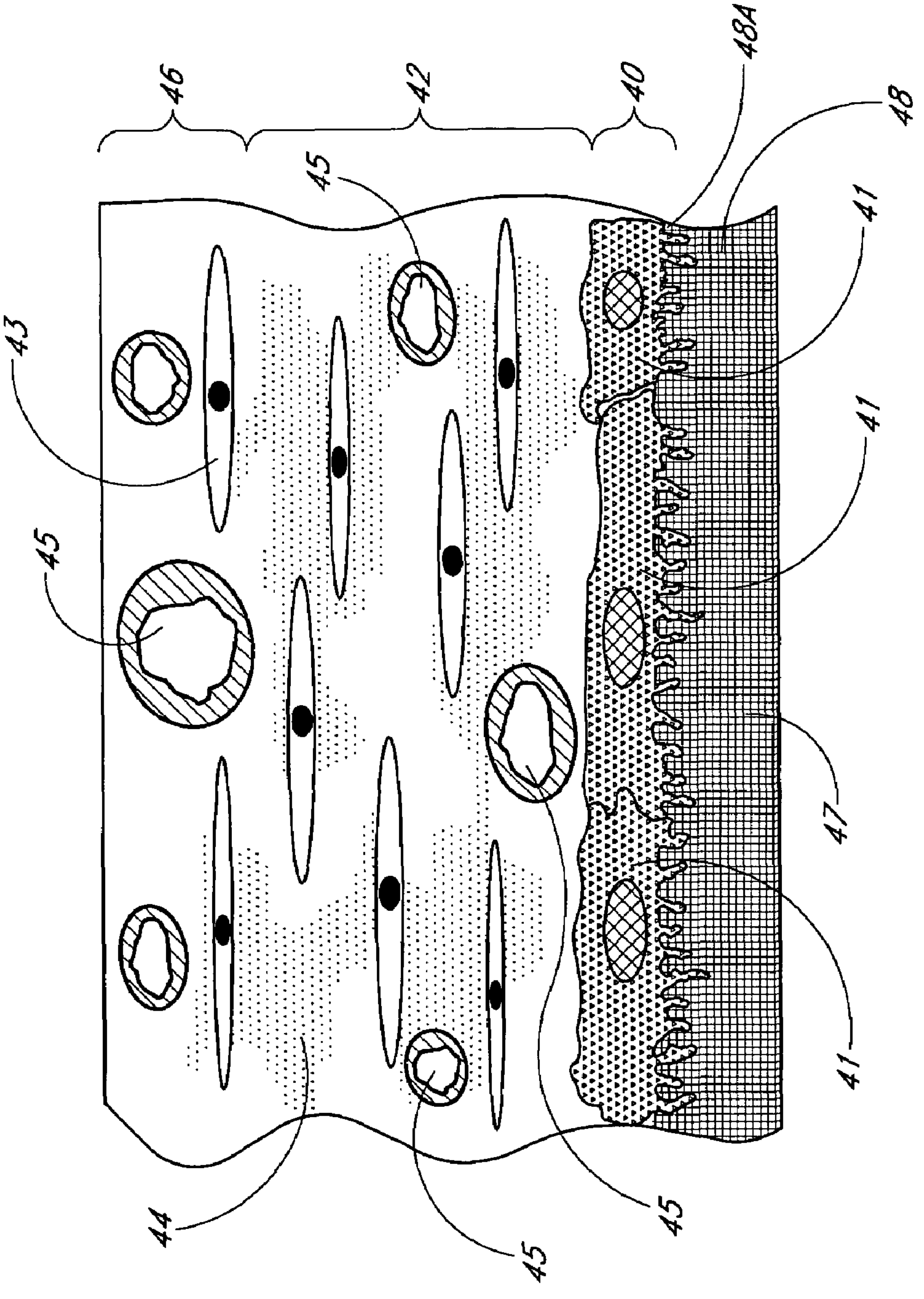
FIG. 2 is an illustration of a device having increased neovascularization within the intermediary layer of the foreign body response.

The present invention relates generally to novel biointerface membranes, their uses with implantable devices and methods for determining analyte levels in a biological fluid. More particularly, the invention provides biointerface membranes that may be utilized with implantable devices and methods for monitoring and determining glucose levels in a biological fluid, a particularly important measurement for individuals having diabetes.

Although the description that follows is primarily directed at glucose monitoring devices including the biointerface membranes of the present invention and methods for their use, these biointerface membranes are not limited to use in devices that measure or monitor glucose. Rather, these biointerface membranes may be applied to a variety of devices, including for example, those that detect and quantify other analytes present in biological fluids (including, but not limited to, cholesterol, amino acids and lactate), especially those analytes that are substrates for oxidase enzymes [see, e.g., U.S. Pat. No. 4,703,756 to Gough et al., hereby incorporated by reference] cell transplantation devices (U.S. Pat. Nos. 6,015,572, 5,964,745 and 6,083,523), drug delivery devices (U.S. Pat. Nos. 5,458,631, 5,820,589 and 5,972,369) and electrical delivery and/or measuring devices such as implantable pulse generation cardiac pacing devices (U.S. Pat. Nos. 6,157,860, 5,782,880 and 5,207,218), electrocardiogram device (U.S. Pat. Nos. 4,625,730 and 5,987,352) and electrical nerve stimulating devices (U.S. Pat. Nos. 6,175,767, 6,055,456 and 4,940,065).

Implantable devices for detecting analyte concentrations in a biological system may utilize the biointerface membranes of the present invention to interfere with the formation of a barrier cell layer, thereby assuring that the sensor receives analyte concentrations representative of that in the vasculature. Drug delivery devices may utilize the biointerface membranes of the present invention to protect the drug housed within the device from host inflammatory or immune cells that might potentially damage or destroy the drug. In addition, the biointerface membrane prevents the formation of a barrier cell layer that might interfere with proper dispensing of drug from the device for treatment of the host. Correspondingly, cell transplantation devices may utilize the biointerface membranes of the present invention to protect the transplanted cells from attack by the host inflammatory or immune response cells while simultaneously allowing nutrients as well as other biologically active molecules needed by the cells for survival to diffuse through the membrane.

The materials contemplated for use in preparing the biointerface membrane also eliminate or significantly delay biodegradation. This is particularly important for devices that continuously measure analyte concentrations. For example, in a glucose-measuring device, the electrode surfaces of the glucose sensor are in contact with (or operably connected with) a thin electrolyte phase, which in turn is covered by a membrane that contains an enzyme, e.g., glucose oxidase, and a polymer system. The biointerface membrane covers this enzyme membrane and serves, in part, to protect the sensor from external forces and factors that may result in biodegradation. By significantly delaying biodegradation at the sensor, accurate data may be collected over long periods of time (e.g. months to years). Correspondingly, biodegradation of the biointerface membrane of implantable cell transplantation devices and drug delivery devices could allow host inflammatory and immune cells to enter these devices, thereby compromising long-term function.

Devices and probes that are implanted into subcutaneous tissue will almost always elicit a foreign body capsule (FBC) as part of the body's response to the introduction of a foreign material. Therefore, implantation of a glucose sensor results in an acute inflammatory reaction followed by building of fibrotic tissue. Ultimately, a mature FBC including primarily a vascular fibrous tissue forms around the device (Shanker and Greisler, Inflammation and Biomaterials in Greco R S, ed. Implantation Biology: The Host Response and Biomedical Devices, pp 68-80, CRC Press (1994)).

In general, the formation of a FBC has precluded the collection of reliable, continuous information because it was previously believed to isolate the sensor of the implanted device in a capsule containing fluid that did not mimic the levels of analytes (e.g. glucose and oxygen) in the body's vasculature. Similarly, the composition of a FBC has prevented stabilization of the implanted device, contributing to motion artifact that also renders unreliable results. Thus, conventionally, it has been the practice of those skilled in the art to attempt to minimize FBC formation by, for example, using a short-lived needle geometry or sensor coatings to minimize the foreign body reaction.

In contrast to conventionally known practice, the teachings of the present invention recognize that FBC formation is the dominant event surrounding long-term implantation of any sensor and must be managed to support rather than hinder or block sensor performance. It has been observed that during the early periods following implantation of an analyte-sensing device, particularly a glucose sensing device, glucose sensors function well. However, after a few days to two or more weeks of implantation, these device lose their function. For example, U.S. Pat. No. 5,791,344 and Gross et al. Performance Evaluation of the Minimed Continuous Monitoring System During Patient home Use", Diabetes Technology and Therapuetics, Vol 2 Number 1, pp 49-56, 2000 have reported a glucose oxidase sensor (that has been approved for use in humans by the Food and Drug Administration) that functioned well for several days following implantation but loses function quickly after 3 days. We have observed similar device behavior with our implantable sensor. These results suggest that there is sufficient vascularization and, therefore, perfusion of oxygen and glucose to support the function of an implanted glucose sensor for the first few days following implantation. New blood vessel formation is clearly not needed for the function of a glucose oxidase mediated electrochemical sensor implanted in the subcutaneous tissue for at least several days after implantation.

We have observed that this lack of sensor function after several days is most likely due to cells, such as polymorphonuclear cells and monocytes that migrate to the wound site during the first few days after implantation. These cells consume glucose and oxygen. If there is an overabundance of such cells, they may deplete the glucose and/or oxygen before it is able to reach the sensor enzyme layer, therefore reducing the sensitivity of the device or rendering it non-functional. After the first few days, further inhibition of device function may be due to cells that associate with the membrane of the device and physically block the transport of glucose into the device (i.e. barrier cells). Increased vascularization would not be expected to overcome barrier cell blockage. The present invention contemplates the use of particular biointerface membrane architectures that interfere with barrier cell layer formation on the membrane's surface. The present invention also contemplates the use of these membranes with a variety of implantable devices (e.g. analyte measuring devices, particularly glucose measuring devices, cell transplantation devices, drug delivery devices and electrical signal delivery and measuring devices).

The sensor interface region refers to the region of a monitoring device responsible for the detection of a particular analyte. For example, in some embodiments of a glucose-monitoring device, the sensor interface refers to that region where a biological sample contacts (directly or after passage through one or more membranes or layers) an enzyme (e.g., glucose oxidase). The sensor interface region may include a biointerface membrane according to the present invention having different domains and/or layers that can cover and protect an underlying enzyme membrane and the electrodes of an implantable analyte-measuring device. In general, the biointerface membranes of the present invention prevent direct contact of the biological fluid sample with the sensor. The membranes only permit selected substances (e.g., analytes) of the fluid to pass therethrough for reaction in the immobilized enzyme domain. The biointerface membranes of the present invention are biostable and prevent barrier cell formation. The characteristics of this biointerface membrane are now discussed in more detail.

I. Biointerface Membrane

Figure 3:
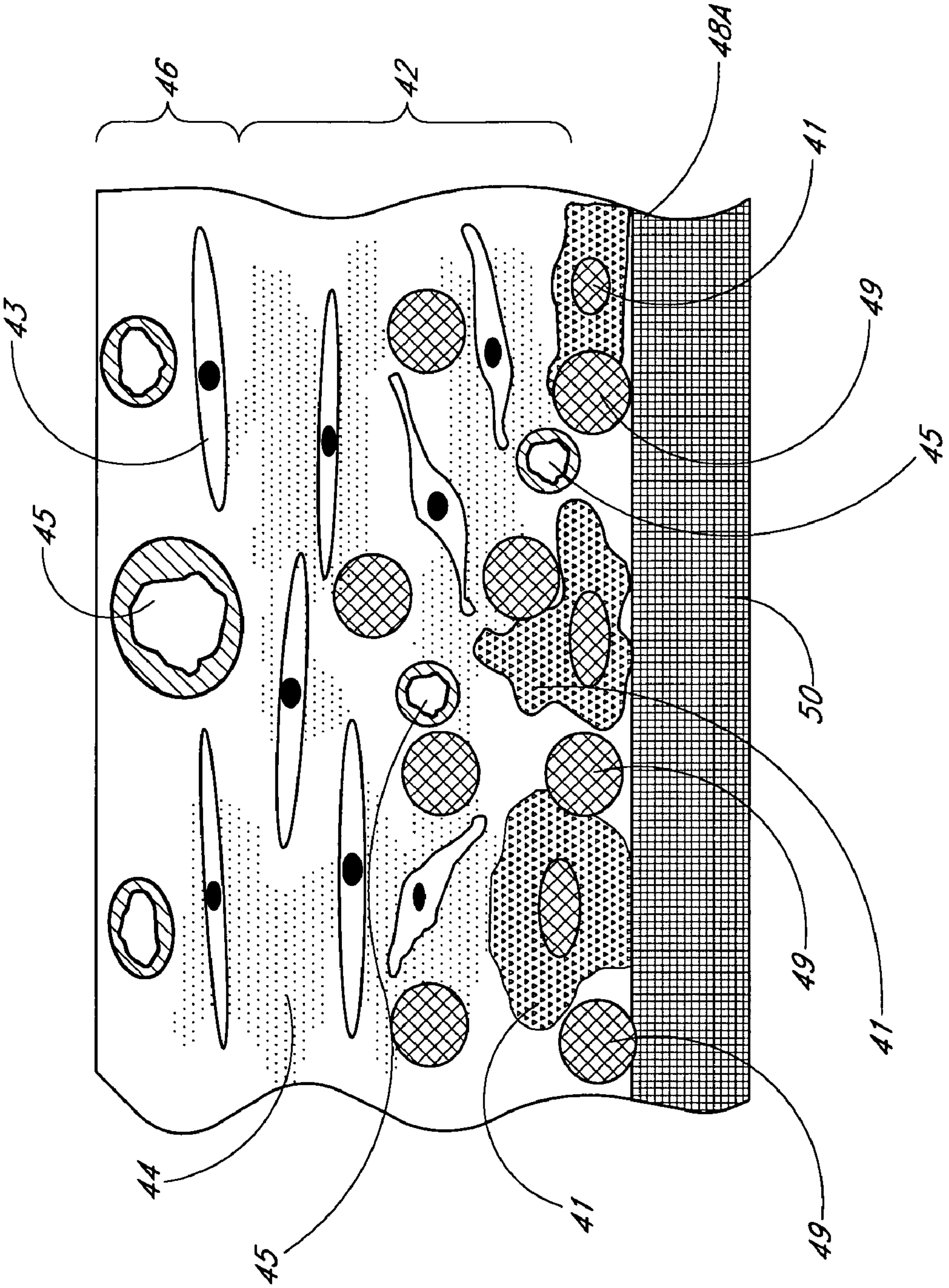
FIG. 3 is an illustration of a membrane of the present invention including a barrier-cell disruptive domain composed of fibers and a cell impermeable domain.

The biointerface membrane is constructed of two or more domains. Referring now to FIG. 3, preferably, the membrane includes a cell impermeable domain 50 proximal to an implantable device, also referred to as the second domain; and a cell disruptive domain, which in the embodiment illustrated includes non-woven fibers 49 distal to an implantable device, also referred to as the first domain.

A. Barrier-Cell Disruptive (First) Domain

Figure 4:
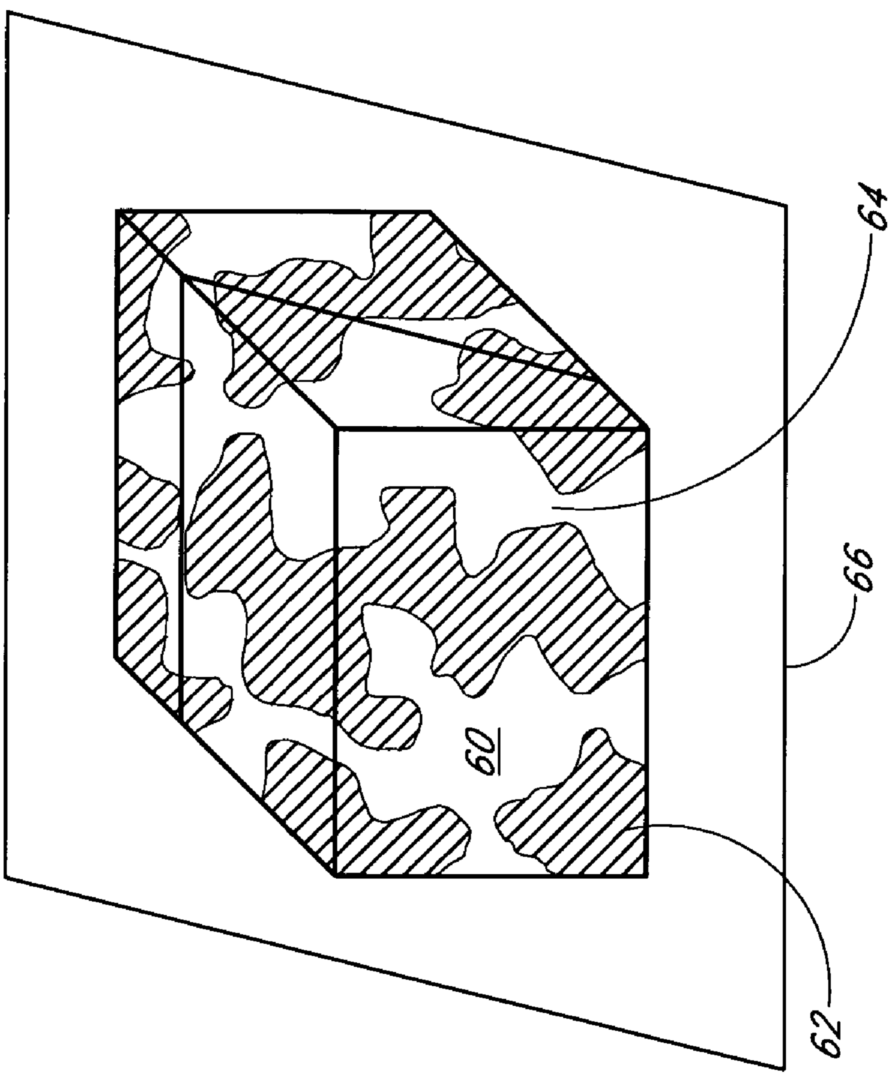
FIG. 4 is an illustration of a three dimensional section of the first domain showing the solid portions and cavities.

As described above, the outermost domain of the inventive membrane includes a material that supports tissue ingrowth. The barrier-cell disruptive domain may be composed of an open-cell configuration having cavities and solid portions. For example, FIG. 4 is an illustration of a three dimensional section 60 of a barrier-cell disruptive domain having solid portions 62 and cavities 64. Cells may enter into the cavities, however, they can not travel through or wholly exist within the solid portions. The cavities allow most substances to pass through, including, e.g., macrophages.

The open-cell configuration yields a co-continuous solid domain that contains greater than one cavity in three dimensions substantially throughout the entirety of the membrane. In addition, the cavities and cavity interconnections may be formed in layers having different cavity dimensions.

Figure 5:
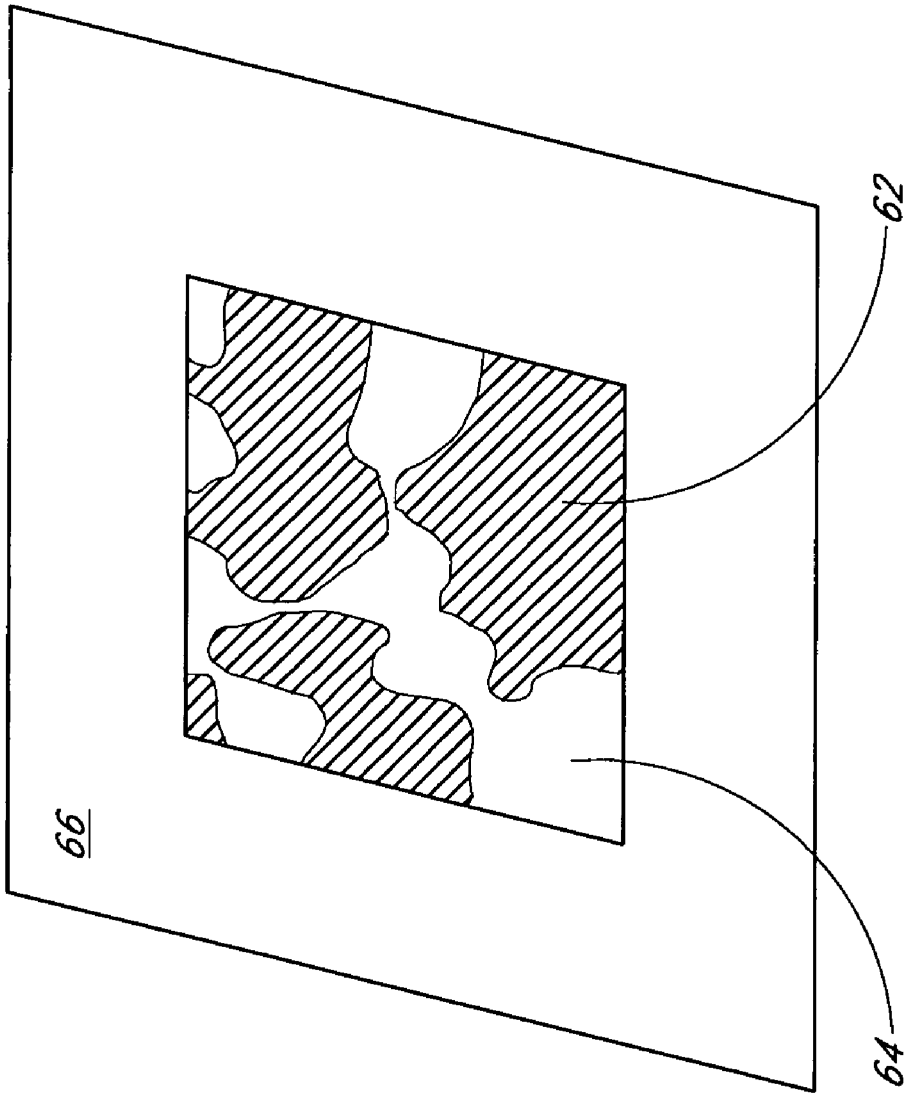
FIG. 5 is an illustration of a cross-section of the first domain in FIG. 4 showing solid portions and cavities.

In order to better describe the dimensions of cavities and solid portions, a two dimensional plane 66 cut through the barrier-cell disruptive domain can be utilized (FIG. 5). A dimension across a cavity 64 or solid portion 62 can be described as a linear line. The length of the linear line is the distance between two points lying at the interface of the cavity and solid portion. In this way, a substantial number of the cavities are not less than 20 microns in the shortest dimension and not more than 1000 microns in the longest dimension. Preferably, a substantial number of the cavities are not less than 25 microns in the shortest dimension and not more than 500 microns in the longest dimension.

Furthermore, the solid portion has not less than 5 microns in a substantial number of the shortest dimensions and not more than 2000 microns in a substantial number of the longest dimensions. Preferably, the solid portion is not less than 10 microns in a substantial number of the shortest dimensions and not more than 1000 microns in a substantial number of the longest dimensions and, most preferably, not less than 10 microns in a substantial number of the shortest dimensions and not more than 400 microns in a substantial number of the longest dimensions.

The solid portion may be comprised of polytetrafluoroethylene or polyethyleneco-tetrafluoroethylene. Preferably, the solid portion includes polyurethanes or block copolymers and, most preferably, is comprised of silicone.

In desired embodiments, the solid portion is composed of porous silicone or non-woven fibers. Non-woven fibers are preferably made from polyester or polypropylene. For example, FIG. 3 illustrates how the non-woven fibers 49 serve to disrupt the continuity of cells, such that they are not able to form a classical foreign body response. All the cell types that are involved in the formation of a FBR may be present. However, they are unable to form an ordered closely opposed cellular monolayer parallel to the surface of the device as in a typical foreign body response to a smooth surface. In this example, the 10-micron dimension provides a suitable surface for foreign body giant cells, but the fibers are in such proximity to allow and foster in growth of blood vessels 45 and vascularize the biointerface region (FIG. 3). Devices with smaller fibers have been used in previous inventions, but such membranes are prone to delamination due to the forces applied by cells in the interstices of the membrane. After delamination, cells are able to form barrier layers on the smooth or microporous surface of the bioprotective layer if it is adhesive to cells or has pores of sufficient size for physical penetration of cell processes, but not of whole cells.

When non-woven fibers are utilized as the solid portion of the present invention, the non-woven fibers may be greater than 5 microns in the shortest dimension. Preferably, the non-woven fibers are about 10 microns in the shortest dimension and, most preferably, the non-woven fibers are greater than or equal to 10 microns in the shortest dimension.

The non-woven fibers may be constructed of polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, polysulfones, and block copolymers thereof including, for example, di-block, tri-block, alternating, random and graft copolymers (block copolymers are discussed in U.S. Pat. Nos. 4,803,243 and 4,686,044, hereby incorporated by reference). Preferably, the non-woven fibers are comprised of polyolefins or polyester or polycarbonates or polytetrafluoroethylene. The thickness of the cell disruptive domain is not less than about 20 microns and not more than about 2000 microns.

B. Cell Impermeable (Second) Domain

The inflammatory response that initiates and sustains a FBC is associated with disadvantages in the practice of sensing analytes. Inflammation is associated with invasion of inflammatory response cells (e.g. macrophages) which have the ability to overgrow at the interface forming barrier cell layers which may block transport across the biointerface membrane. These inflammatory cells may also biodegrade many artificial biomaterials (some of which were, until recently, considered nonbiodegradable). When activated by a foreign body, tissue macrophages degranulate, releasing from their cytoplasmic myeloperoxidase system hypochlorite (bleach) and other oxidative species. Hypochlorite and other oxidative species are known to break down a variety of polymers. However, polycarbonate based polyurethanes are believed to be resistant to the effects of these oxidative species and have been termed biodurable. In addition, because hypochlorite and other oxidizing species are short-lived chemical species in vivo, biodegradation will not occur if macrophages are kept a sufficient distance from the enzyme active membrane.

The present invention contemplates the use of cell impermeable biomaterials of a few microns thickness or more (i.e., a cell impermeable domain) in most of its membrane architectures. Desirably, the thickness of the cell impermeable domain is not less than about 10 microns and not more than about 100 microns. This domain of the biointerface membrane is permeable to oxygen and may or may not be permeable to glucose and is constructed of biodurable materials (e.g. for period of several years in vivo) that are impermeable by host cells (e.g. macrophages) such as, for example, polymer blends of polycarbonate based polyurethane and PVP.

The innermost domain of the inventive membrane is non-adhesive for cells (i.e. the cell impermeable domain), which is in contrast to the inventions of Brauker et al. (supra), and Shults et al. (supra). In both of these previous patents, examples are provided in which the cellimpenetrable membrane (Brauker et al.) or biointerface membrane (Shults et al.) are derived from a membrane known as Biopore.™. as a cell culture support sold by Millipore (Bedford, Mass.). In the presence of certain extracellular matrix molecules, and also in vivo, many cell types are able to strongly adhere to this membrane making it incapable of serving as a non-adhesive domain. Further, since they allow adherence of cells to the innermost layer of the membrane they promote barrier cell layer formation that decreases the membranes ability to transport molecules across the device-tissue interface. Moreover, when these cells multiply, they ultimately cause pressure between the membrane layers resulting in delamination of the layers and catastrophic failure of the membrane.

As described above, in one embodiment of the inventive membrane, the second domain is resistant to cellular attachment and is impermeable to cells and preferably composed of a biostable material. The second domain may be formed from materials such as those previously listed for the first domain and as copolymers or blends with hydrophilic polymers such as polyvinylpyrrolidone (PVP), polyhydroxyethyl methacrylate, polyvinylalcohol, polyacrylic acid, polyethers, such as polyethylene glycol, and block copolymers thereof including, for example, di-block, tri-block, alternating, random and graft copolymers (block copolymers are discussed in U.S. Pat. Nos. 4,803,243 and 4,686,044, hereby incorporated by reference).

Preferably, the second domain is comprised of a polyurethane and a hydrophilic polymer. Desirably, the hydrophilic polymer is polyvinylpyrrolidone. In one embodiment of this aspect of the invention, the second domain is polyurethane comprising not less than 5 weight percent polyvinylpyrrolidone and not more than 45 weight percent polyvinylpyrrolidone. Preferably, the second domain comprises not less than 20 weight percent polyvinylpyrrolidone and not more than 35 weight percent polyvinylpyrrolidone and, most preferably, polyurethane comprising about 27 weight percent polyvinylpyrrolidone.

As described above, in one desired embodiment the cell impermeable domain is comprised of a polymer blend comprised of a non-biodegradable polyurethane comprising polyvinylpyrrolidone. This prevents adhesion of cells in vitro and in vivo and allows many molecules to freely diffuse through the membrane. However, this domain prevents cell entry or contact with device elements underlying the membrane, and prevents the adherence of cells, and thereby prevents the formation of a barrier cell layer.

II. Implantable Glucose Monitoring Devices Using the Biointerface Membranes of the Present Invention The present invention contemplates the use of unique membrane architectures around the sensor interface of an implantable device. However, it should be pointed out that the present invention does not require a device including particular electronic components (e.g., electrodes, circuitry, etc). Indeed, the teachings of the present invention can be used with virtually any monitoring device suitable for implantation (or subject to modification allowing implantation); suitable devices include, analyte measuring devices, cell transplantation devices, drug delivery devices, electrical signal delivery and measurement devices and other devices such as those described in U.S. Pat. Nos. 4,703,756 and 4,994,167 to Shults et al.; U.S. Pat. No. 4,703,756 to Gough et al., and U.S. Pat. No. 4,431,004 to Bessman et al.; the contents of each being hereby incorporated by reference, and Bindra et al., Anal. Chem. 63:1692-96 (1991).

Figure 6A:
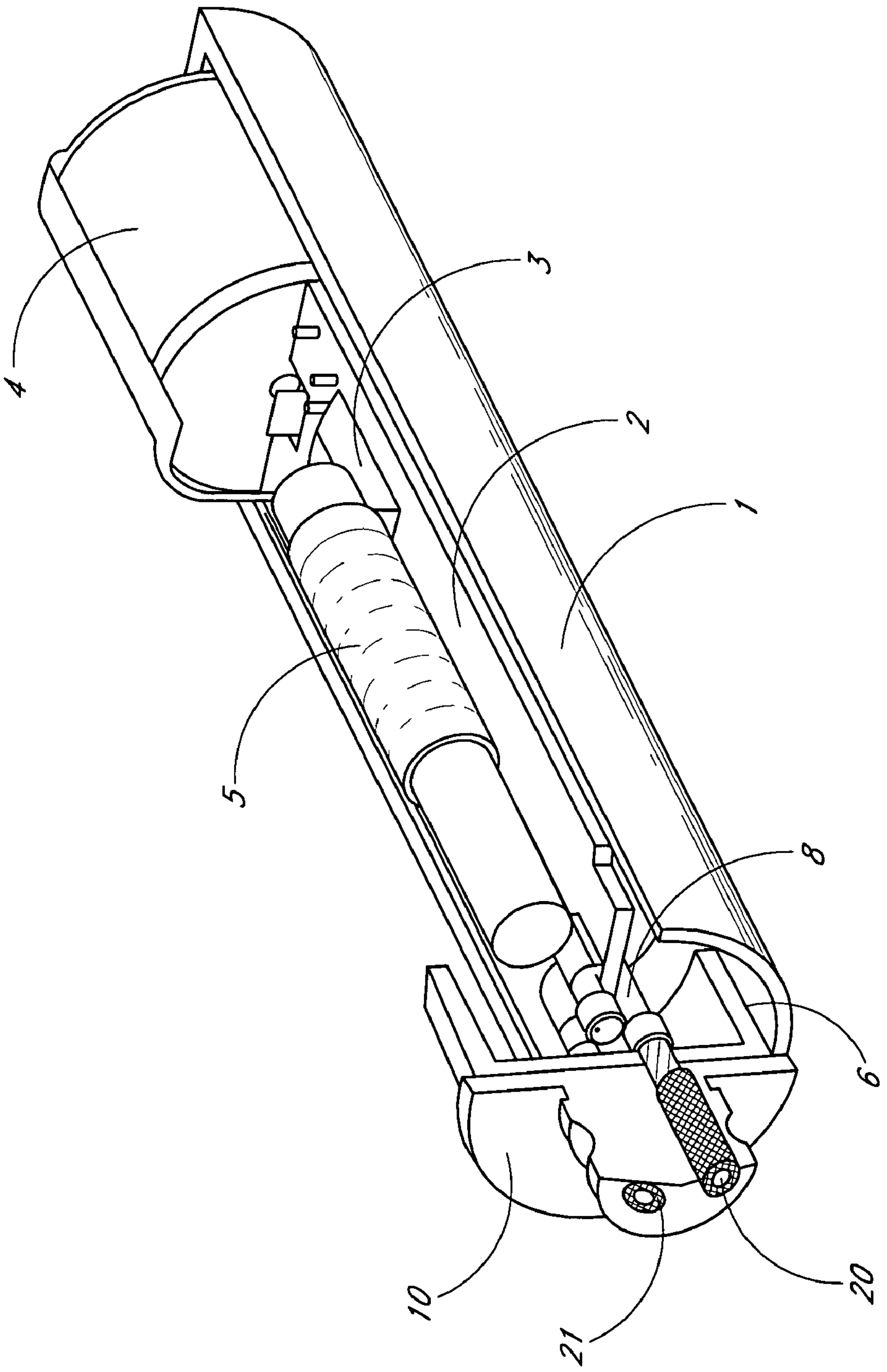
FIG. 6A depicts a cross-sectional drawing of one embodiment of an implantable analyte measuring device for use in combination with a membrane according to the present invention.

We refer now to FIG. 6A, which shows a preferred embodiment of an analyte measuring device for use in combination with a membrane according to the present invention. In this embodiment, a ceramic body 1 and ceramic head 10 houses the sensor electronics that include a circuit board 2, a microprocessor 3, a battery 4, and an antenna 5. Furthermore, the ceramic body 1 and head 10 possess a matching taper joint 6 that is sealed with epoxy. The electrodes are subsequently connected to the circuit board via a socket 8.

Figure 6B:
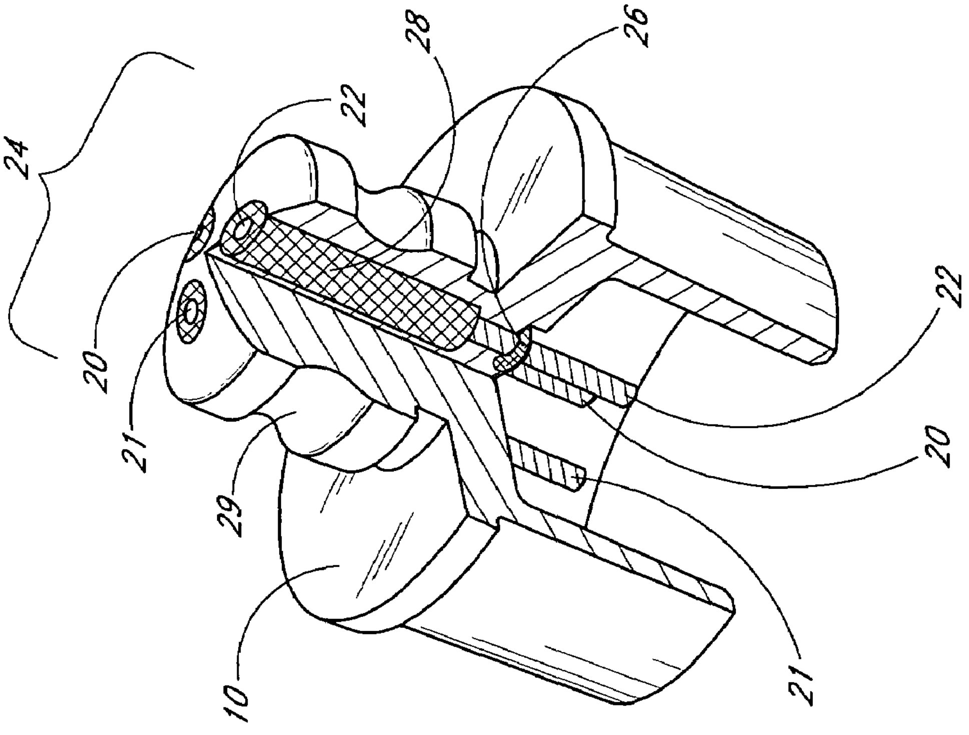
FIG. 6B depicts a cross-sectional exploded view of the sensor head shown in FIG. 6A.

As indicated in detail in FIG. 6B, three electrodes protrude through the ceramic head 10, a platinum working electrode 21, a platinum counter electrode 22 and a silver/silver chloride reference electrode 20. Each of these is hermetically brazed 26 to the ceramic head 10 and further affixed with epoxy 28. The sensing region 24 is covered with the sensing membrane described below and the ceramic head 10 contains a groove 29 so that the membrane may be affixed into place with an o-ring.

Figure 6C:
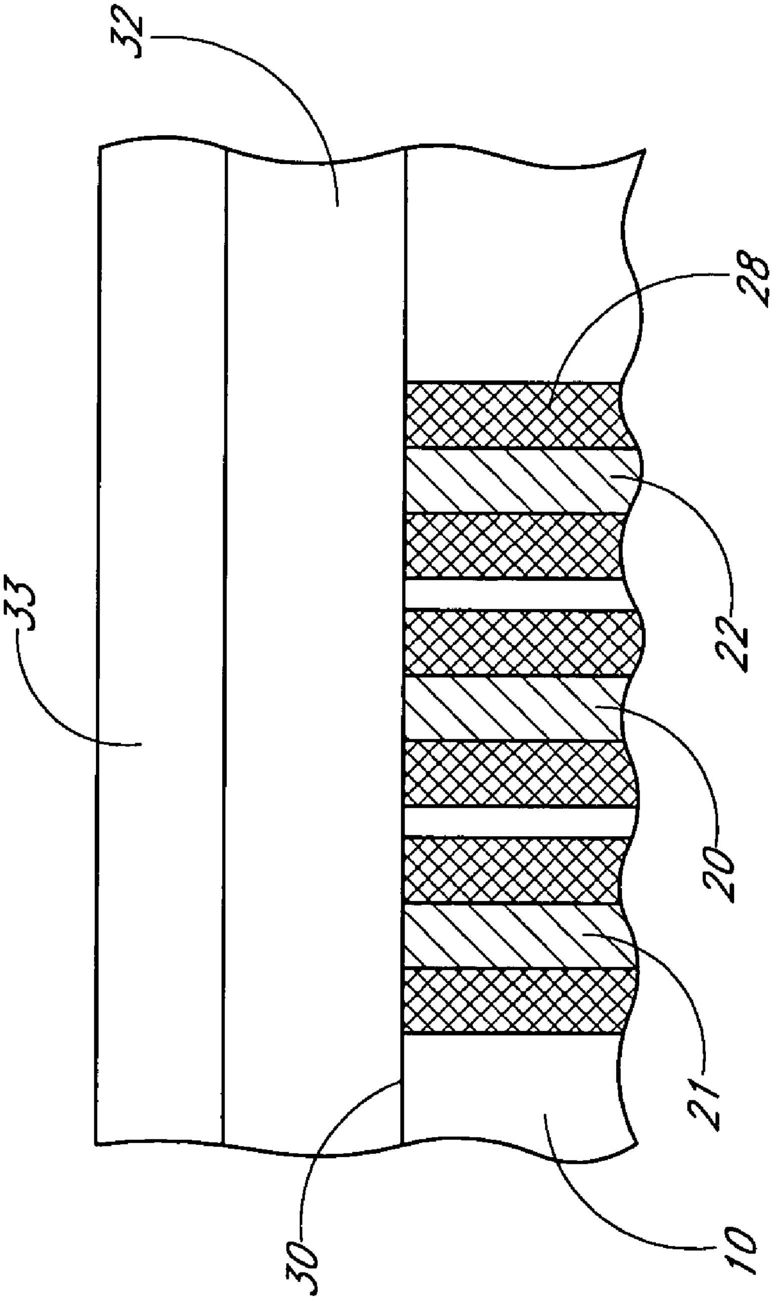
FIG. 6C depicts a cross-sectional exploded view of the electrode-membrane region set forth in FIG. 6B.

FIG. 6C depicts a cross-sectional exploded view of the electrode-membrane region 24 set forth in FIG. 6B detailing the sensor tip and the functional membrane layers. As depicted in FIG. 6C, the electrode-membrane region includes the inventive biointerface membrane 33 and a sensing membrane 32. The top ends of the electrodes are in contact with the electrolyte phase 30, a free-flowing fluid phase. The electrolyte phase is covered by the sensing membrane 32 that includes an enzyme, e.g., glucose oxidase. In turn, the inventive interface membrane 33 covers the enzyme membrane 32 and serves, in part, to protect the sensor from external forces that may result in environmental stress cracking of the sensing membrane 32.

III. Experimental

The following examples serve to illustrate certain preferred embodiments and aspects of the present invention and are not to be construed as limiting the scope thereof In the preceding description and the experimental disclosure which follows, the following abbreviations apply: Eq and Eqs (equivalents); mEq (milliequivalents); M (molar); mM (millimolar) .mu·M (micromolar); N (Normal); mol (moles); mmol (millimoles); .mu·mol (micromoles); nmol (nanomoles); g (grams); mg (milligrams); .mu·g (micrograms); Kg (kilograms); L (liters); mL (milliliters); dL (deciliters); .mu·L (microliters); cm (centimeters); mm (millimeters); .mu·m (micrometers); nm (nanometers); h and hr (hours); min. (minutes); s and sec. (seconds); .degree. C. (degrees Centigrade); Astor Wax (Titusville, Pa.); BASF Wyandotte Corporation (Parsippany, N.J.); Data Sciences, Inc. (St. Paul, Minn.); Douglas Hansen Co., Inc. (Minneapolis, Minn.); DuPont (DuPont Co., Wilmington, Del.); Exxon Chemical (Houston, Tex.); GAF Corporation (New York, N.Y.); Markwell Medical (Racine, Wis.); Meadox Medical, Inc. (Oakland, N.J.); Mobay (Mobay Corporation, Pittsburgh, Pa.); Sandoz (East Hanover, N.J.); and Union Carbide (Union Carbide Corporation; Chicago, Ill.).

Example 1

Preparation of Biointerface Membrane with Non-Woven Fibers

The barrier-cell disruptive domain may be prepared from a non-woven polyester fiber filtration membrane. The cell-impermeable domain may then be coated on this domain layer. The cell-impermeable domain was prepared by placing approximately 706 gm of dimethylacetamide (DMAC) into a 3 L stainless steel bowl to which a polycarbonateurethane solution (1325 g, Chronoflex AR 25% solids in DMAC and a viscosity of 5100 cp) and polyvinylpyrrolidone (125 g, Plasdone K-90D) were added. The bowl was then fitted to a planetary mixer with a paddle type blade and the contents were stirred for 1 hour at room temperature. This solution was then coated on the barrier-cell disruptive domain by knife-edge drawn at a gap of 0.006" and dried at 60.degree. C. for 24 hours. The membrane is then mechanically secured to the sensing device by an O-ring.

Example 2

Preparation of Biointerface Membrane with Porous Silicone

The barrier-cell disruptive domain can be comprised of a porous silicone sheet. The porous silicone was purchased from Seare Biomatrix Systems, Inc. The cell-impermeable domain was prepared by placing approximately 706 gm of dimethylacetamide (DMAC) into a 3 L stainless steel bowl to which a polycarbonateurethane solution (1,325 gm, Chronoflex AR 25% solids in DMAC and a viscosity of 5100 cp) and polyvinylpyrrolidone (125 gm, Plasdone K-90D) were added. The bowl was then fitted to a planetary mixer with a paddle type blade and the contents were stirred for 1 hour at room temperature. The cell-impermeable domain coating solution was then coated onto a PET release liner (Douglas Hansen Co.) using a knife over roll set at a 0.012" gap. This film was then dried at 305.degree. F. The final film was approximately 0.0015" thick. The biointerface membrane was prepared by pressing the porous silicone onto the cast cell-impermeable domain. The membrane is then mechanically secured to the sensing device by an O-ring.

Example 3

Test Method for Glucose Measuring Device Function

In vivo sensor function was determined by correlating the sensor output to blood glucose values derived from an external blood glucose meter. We have found that non-diabetic dogs do not experience rapid blood glucose changes, even after ingestion of a high sugar meal. Thus, a 10% dextrose solution was infused into the sensor-implanted dog. A second catheter is placed in the opposite leg for the purpose of blood collection. The implanted sensor was programmed to transmit at 30-second intervals using a pulsed electromagnet. A dextrose solution was infused at a rate of 9.3 ml/minute for the first 25 minutes, 3.5 ml/minute for the next 20 minutes, 1.5 ml/minute for the next 20 minutes, and then the infusion pump was powered off Blood glucose values were measured in duplicate every five minutes on a blood glucose meter (LXN Inc., San Diego, Calif.) for the duration of the study. A computer collected the sensor output. The data was then compiled and graphed in a spreadsheet, time aligned, and time shifted until an optimal R-squared value was achieved. The R-squared value reflects how well the sensor tracks with the blood glucose values.

Example 4

In Vivo Evaluation of Glucose Measuring Devices Including the Biointerface Membranes of the Present Invention To test the importance of a cell-disruptive membrane, implantable glucose sensors comprising the biointerface membranes of the present invention were implanted into dogs in the subcutaneous tissues and monitored for glucose response on a weekly basis. Control devices comprising only a cell-impermeable domain ("Control") were compared with devices comprising a cell-impermeable domain and a barrier-cell disruptive domain, in particular, wherein the barrier-cell disruptive domain was either a non-woven fiber ("Non-Woven Fibers") or porous silicone ("Porous Silicone").

Figure 7:
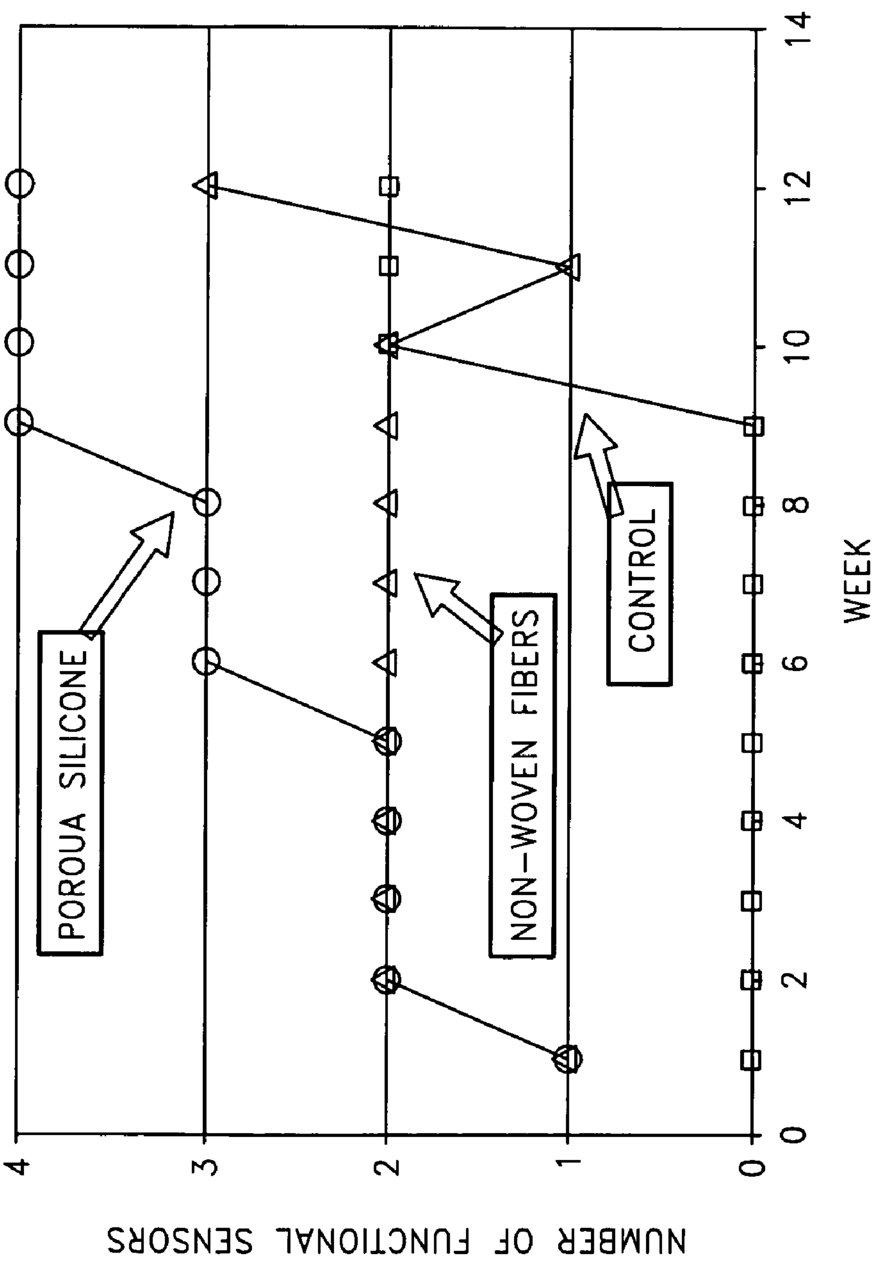
FIG. 7 is a graphical representation of the number of functional sensors versus time (i.e. weeks) comparing control devices including only a cell-impermeable domain ("Control"), with devices including a cell-impermeable domain and a barrier-cell domain, in particular, wherein the barrier-cell disruptive domain includes non-woven fiber ("Non-Woven Fibers") and wherein the barrier-cell disruptive domain includes porous silicone ("Porous Silicone").

Four devices from each condition were implanted subcutaneously in the ventral abdomen of normal dogs. On a weekly basis, the dogs were infused with glucose as described in Example 3 in order to increase their blood glucose levels from about 120 mg/dl to about 300 mg/dl. Blood glucose values were determined with a LXN blood glucose meter at 5-minute intervals. Sensor values were transmitted at 0.5-minute intervals. Regression analysis was done between blood glucose values and the nearest sensor value within one minute. Devices that yielded an R-squared value greater than 0.5 were considered functional. FIG. 7 shows, for each condition, the number of functional devices over the 12-week period of the study. Both test devices performed better than the control devices over the first 9 weeks of the study. All of the porous silicone devices were functional by week 9. Two of 4 polypropylene fiber devices were functional by week 2, and 3 of 4 were functional on week 12. In contrast, none of the control devices were functional until week 10, after which 2 were functional for the remaining 3 weeks. These data clearly show that the use of a cell-disruptive layer in combination with a cell-impermeable layer improves the function of implantable glucose sensors.

The description and experimental materials presented above are intended to be illustrative of the present invention while not limiting the scope thereof It will be apparent to those skilled in the art that variations and modifications can be made without departing from the spirit and scope of the present invention.

What is claimed is:

1. A biointerface membrane, the membrane comprising:

a first domain, wherein the first domain comprises a solid portion having a plurality of interconnected cavities therein that form an architecture that supports tissue in ingrowth and interferes with barrier cell layer formation, wherein the solid portion comprises silicone; and a second domain, wherein the second domain is permeable to the passage of an analyte and is impermeable to cells or cell processes.

2. The biointerface membrane according to claim 1, wherein the cavities form a cavernous configuration with greater than one cavity in three dimensions substantially throughout the entirety of the first domain.

3. The biointerface membrane according to claim 2, wherein the cavities are formed in a plurality of layers, each layer having different cavity dimensions.

4. The biointerface membrane according to claim 1, wherein a substantial number of the cavities are from about 20 microns to about 2000 microns in at least one dimension.

5. The biointerface membrane according to claim 1, wherein a substantial number of the cavities are from about 25 microns to about 1000 microns in at least one dimension.

6. The biointerface membrane according to claim 1, wherein the second domain comprises a biostable material.

7. The biointerface membrane according to claim 6, wherein the biostable material comprises a hydrophobic portion and a hydrophilic portion.

8. The biointerface membrane according to claim 6, wherein the biostable material comprises polyurethane.

9. The biointerface membrane according to claim 6, wherein the biostable material comprises polyurethane and a hydrophilic polymer.

10. The biointerface membrane according to claim 6, wherein the biostable material comprises polyurethane and polyvinylpyrrolidone.

11. The biointerface membrane according to claim 6, wherein the bio stable material comprises silicone and a hydrophilic component.

12. The biointerface membrane according to claim 6, wherein the biostable material comprises silicone and polyethylene glycol.

13. An implantable device, the device comprising a biointerface membrane, the membrane comprising a first domain and a second domain, wherein the first domain is distal to the implantable device, wherein the first domain comprises a solid portion comprising silicone and having a plurality of interconnected cavities therein that form a cavernous configuration with greater than one cavity in three dimensions substantially throughout the entirety of the first domain, wherein the second domain is proximal to the implantable device, and wherein the second domain is permeable to the passage of a chemical and is impermeable to cells or cell processes.

14. The implantable device of claim 13, comprising an analyte sensor.

15. The implantable device of claim 13, comprising a glucose sensor.

16. The implantable device of claim 13, comprising a cell transplantation device.

17. The implantable device of claim 13, comprising a drug delivery device.

18. The implantable device of claim 17, wherein the drug delivery device is selected from the group consisting of a pump, a microcapsule, and a macrocapsule.

19. The implantable device of claim 13, comprising an electrical signal measuring device.

20. The implantable device of claim 13, comprising an electrical pulse delivering device.

21. A method of monitoring an analyte level, the method comprising:

implanting an implantable analyte sensor in a host, the sensor comprising a biointerface membrane, the membrane comprising a first domain and a second domain, wherein the first domain is distal to the implantable device, wherein the first domain comprises a solid portion comprising silicone and having a plurality of interconnected cavities therein that form an architecture that supports tissue ingrowth and interferes with barrier cell layer formation, wherein the second domain is proximal to the implantable device, and wherein the second domain is permeable to the passage of an analyte and is impermeable to cells or cell processes; and monitoring an analyte level.

22. The method according to claim 21, wherein implanting the sensor in the host comprises implanting the sensor in a subcutaneous tissue of a host.

23. The method according to claim 21, wherein the analyte sensor is configured to permit accurate continuous analyte sensing.

24. The method according to claim 21, wherein implanting the sensor in the host comprises implanting the sensor in a subcutaneous tissue of a host.

25. An implantable device, the device comprising:

a membrane, the membrane comprising a biointerface region comprising a cavernous first portion and a non-cavernous second portion, wherein the non-cavernous second portion is resistant to cellular attachment, cells, or cell processes, and wherein the non-cavernous second portion is permeable to the passage of at least one chemical, wherein the cavernous first portion comprises a plurality of interconnected cavities and has greater than one cavity in three dimensions substantially throughout the entirety of the cavernous first portion.

26. The implantable device according to claim 25, wherein the cavernous first portion comprises a solid portion formed with the plurality of interconnected cavities therein and configured to support tissue ingrowth and interfere with barrier cell layer formation.

27. The implantable device according to claim 25, wherein a substantial number of the cavities are from about 20 microns to about 2000 microns in at least one dimension.

28. The implantable device according to claim 25, wherein a substantial number of the cavities are from about 25 microns to about 1000 microns in at least one dimension.

29. The implantable device according to claim 25, wherein the cavities are formed in a plurality of layers, each layer having different cavity dimensions.

30. The implantable device according to claim 25, wherein the second portion comprises a biostable material.

31. The implantable device according to claim 30, wherein the biostable material comprises a hydrophobic portion and a hydrophilic portion.

32. The implantable device according to claim 30, wherein the biostable material comprises polyurethane.

33. The implantable device according to claim 30, wherein the biostable material comprises polyurethane and a hydrophilic polymer.

34. The implantable device according to claim 30, wherein the biostable material comprises polyurethane and polyvinylpyrrolidone.

35. The implantable device according to claim 30, wherein the biostable material comprises silicone and a hydrophilic component.

36. The implantable device according to claim 30, wherein the first portion comprises silicone.

37. The implantable device according to claim 25, wherein the device comprises an implantable glucose sensor.

38. The implantable device according to claim 25, wherein the device comprises a cell transplantation device.

39. The implantable device according to claim 25, wherein the device comprises a drug delivery device.

40. The implantable device according to claim 39, wherein the drug delivery device is selected from the group consisting of a pump, a microcapsule, and a macrocapsule.

41. The implantable device according to claim 25, wherein the device comprises an electrical signal measuring device.

42. The implantable device according to claim 25, wherein the device comprises an electrical pulse delivering device.

43. An implantable glucose sensor, the sensor comprising:

a porous silicone portion;

a non-porous skin, wherein the non-porous skin is adjacent to the porous silicone portion, and wherein the non-porous skin is permeable to glucose and is impermeable to cells or cell processes; and a glucose measuring device.

44. An implantable sensor, the sensor comprising:

a porous membrane comprising silicone and configured to allow cells and cell processes to pass through;

a non-porous membrane that is permeable to analytes and impermeable to cells and cell processes; and an analyte measuring device.

45. An implantable glucose sensor, the sensor comprising:

a fibrous domain that supports tissue ingrowth and configured to allow cells and cell processes to pass through;

a non-fibrous domain, wherein the non-fibrous domain is adjacent to the fibrous domain, and wherein the non-fibrous domain is permeable to analytes and is impermeable to cells or cell processes; and a glucose measuring device.

* * * * *

UNITED STATES PATENT AND TRADEMARK OFFICE

CERTIFICATE OF CORRECTION

PATENT NO. : 7,632,228 B2
APPLICATION NO. : 10/768889
DATED : December 15, 2009
INVENTOR(S) : Brauker et al.

It is certified that error appears in the above-identified patent and that said Letters Patent is hereby corrected as shown below:

| Issued Patent Column | Line | 1. Description of Discrepancy |
|---|---|---|
| Title page (Item 56) Page 5 Col. 1 | 43 | Under Other Publications, change "Bromedical" to --Biomedical--. |
| Title page (Item 56) Page 5 Col. 1 | 47 | Under Other Publications, change "208-" to --298- --. |
| Title page (Item 56) Page 5 Col. 2 | 54 | Under Other Publications, change "Voltammetryand" to --Voltammetry and--. |
| Title page (Item 56) Page 6 Col. 1 | 51 | Under Other Publications, change "Aniodic" to --Anodic--. |
| Title page (Item 56) Page 6 Col. 1 | 54 | Under Other Publications, change "lshikawa," to --Ishikawa,--. |
| Title page (Item 56) Page 6 Col. 1 | 54 | Under Other Publications, change "290-microm" to --290-micron--. |
| Title page (Item 56) Page 7 Col. 2 | 39 | Under Other Publications, change "El" to --EI--. |
| Title page (Item 56) Page 7 Col. 2 | 48 | Under Other Publications, change "wtih" to --with--. |
| Title page (Item 56) Page 7 Col. 2 | 69 | Under Other Publications, change "Hoeld," to --Hoeld,--. |
| Title page (Item 56) Page 8 Col. 2 | 71 | Under Other Publications, change "Membran," to --Membrane,--. |

Signed and Sealed this

Twenty-second Day of June, 2010

David J. Kappos
*Director of the United States Patent and Trademark Office*

| | | |
|---|---|---|
| Title page (Item 56) Page 9 Col. 2 | 21 | Under Other Publications, change “Fianal” to --Final--. |
| 2 | 3 | Change “(<1.0 .mu·m)” to --(<1.0 .mu.m)--. |
| 2 | 15 | Change “Avgoustiniatos” to --Augoustiniatos--. |
| 5 | 43 | Change “H.sub.2O.sub.2-.” to --H.sub.2O.sub.2.--. |
| 7 | 62 | Change “Therapuetics,” to --Therapeutics,--. |
| 10 | 43 | Change “Biopore.™.” to --Biopore$^{TM}$--. |
| 11 | 57 | Change “o-ring.” to --O-ring.--. |
| 12 | 8 | After “thereof” insert --.--. |
| 12 | 12 | Change “.mu·M” to --.mu.M--. |
| 12 | 13 | Change “.mu·mol” to --.mu.mol--. |
| 12 | 14 | Change “.mu·g” to --.mu.g--. |
| 12 | 16 | Change “.mu·L” to --.mu.L--, |
| 12 | 17 | Change “.mu·m” to --.mu.m--. |
| 14 | 6 | Change “thereof” to --thereof.--. |
| 14 | 14 | In Claim 1, after “tissue” delete “in”. |
| 14 | 47 | In Claim 11, change “bio stable” to --biostable--. |
| 16 | 36 | In Claim 43, change “portion;” to --portion configured to allow cells and cell processes to pass through;--. |

UNITED STATES PATENT AND TRADEMARK OFFICE

CERTIFICATE OF CORRECTION

PATENT NO. : 7,632,228 B2
APPLICATION NO. : 10/768889
DATED : December 15, 2009
INVENTOR(S) : Brauker et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1721 days.

Signed and Sealed this

Twenty-first Day of December, 2010

David J. Kappos

*Director of the United States Patent and Trademark Office*

(12) EX PARTE REEXAMINATION CERTIFICATE (8562nd)
United States Patent
Brauker et al.

(10) Number: US 7,632,228 C1
(45) Certificate Issued: Sep. 20, 2011

(54) MEMBRANE FOR USE WITH IMPLANTABLE DEVICES

(75) Inventors: James H. Brauker, San Diego, CA (US); Mark C. Shults, Madison, WI (US); Mark A. Tapsak, San Diego, CA (US)

(73) Assignee: Dexcom, Inc., San Diego, CA (US)

Reexamination Request:
No. 90/011,080, Jul. 2, 2010

Reexamination Certificate for:
Patent No.: 7,632,228
Issued: Dec. 15, 2009
Appl. No.: 10/768,889
Filed: Jan. 29, 2004

Certificate of Correction issued Jun. 22, 2010.

Certificate of Correction issued Dec. 21, 2010.

Related U.S. Application Data

(63) Continuation of application No. 09/916,386, filed on Jul. 27, 2001, now Pat. No. 6,702,857.

(51) Int. Cl.
*A61B 5/00* (2006.01)
*A61F 2/02* (2006.01)
*G01N 27/40* (2006.01)

(52) U.S. Cl. .................... 600/309; 600/345; 600/347; 623/23.76; 204/403.07; 204/415

(58) Field of Classification Search .................... 600/309
See application file for complete search history.

(56) References Cited

U.S. PATENT DOCUMENTS 5,706,807 A 1/1998 Picha

FOREIGN PATENT DOCUMENTS

WO WO 98/38906 9/1998
WO WO 00/13003 * 3/2000

OTHER PUBLICATIONS

Amato et al., Jun. 1989, Experience with the Polytetrafluoroethylene Surgical Membrane for Pericardial Closure in Operations for Congenital Cardiac Defects, J Thorac Cardiovasc Surg., 97(6): 929–934.

Copeland et al., Jun. 2001, Synthetic Membrane Neo–Pericardium Facilitates Total Artificial Heart Explantation, J Heart and Lung Transpl., 20(6): 654–656.

Gore Preclude® Pericardial Membrane Brochure, Jun. 2009, W.L. Gore & Associates, Inc., Flagstaff, AZ 86004.

Harada et al., Nov. 1988, Long–term Results of the Clinical Use of an Expanded Polytetrafluoroethylene Surgical Membrance as a Pericardial Substitute, J Thorac Cardovasc Surg., 96(5): 811–815.

Heydorn et al., Aug. 1987, A New Look at Pericardial Substitutes, J Thorac Cardiovasc Surg., 94(2): 291–296.

(Continued)

*Primary Examiner* — Jeanne M Clark

(57) ABSTRACT

The present invention provides a biointerface membrane for use with an implantable device that interferes with the formation of a barrier cell layer including; a first domain distal to the implantable device wherein the first domain supports tissue attachment and interferes with barrier cell layer formation and a second domain proximal to the implantable device wherein the second domain is resistant to cellular attachment and is impermeable to cells. In addition, the present invention provides sensors including the biointerface membrane, implantable devices including these sensors or biointerface membranes, and methods of monitoring glucose levels in a host utilizing the analyte detection implantable device of the invention. Other implantable devices which include the biointerface membrane of the present invention, such as devices for cell transplantation, drug delivery devices, and electrical signal delivery or measuring devices are also provided.

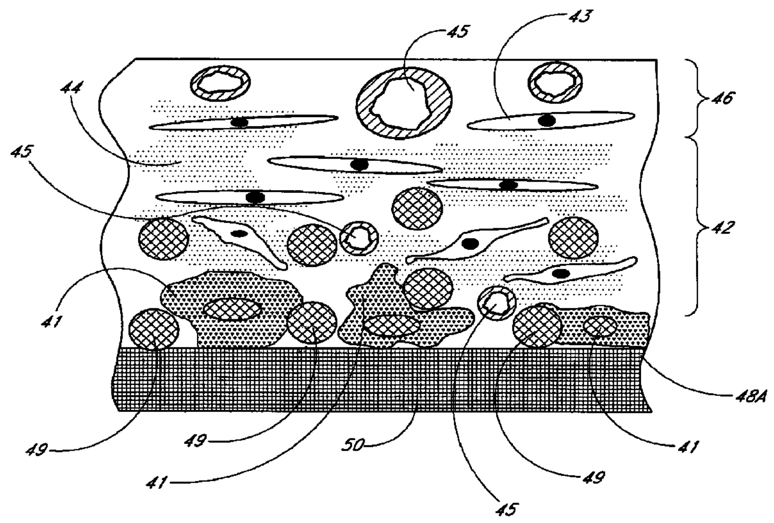

OTHER PUBLICATIONS

Leprince et al., Jan. 2001, Expanded Polytetrafluoroethylene Membranes to Wrap Surfaces of Circulatory Support Devices in Patients Undergoing Bridge to Heart Transplantation, Eu J Cardiothor Surg 19: 302–306.

Loebe et al., 1993, Use of Polytetrafluoroethylene Surgical Membrance as a Pericardial Substitute, PTFE Membrane in Correction of Congenital Heart Defects—Texas Heart Institute Journal 20(3): 213–217.

Minale et al., Sep. 1988, Clinical Experience with Expanded Plytetrafluoroethylene Gore–Tex® Surgical Membrane for Pericardial Closure: A Study of 110 Cases, J Card Surg., 3(3): 193–201.

Preclude® Pericardial Membrane Brochure, Nov. 2001, W.L. Gore & Associates, Inc., Flagstaff, AZ 86004.

Revuelta et al., Mar. 1985, Expanded Polytetrafluoroethylene Surgical Membrance for Pericardial Closure, J Thorac Cardiovasc Surg., 89(3): 451–455.

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 13 and 16 are determined to be patentable as amended.

Claims 14, 15 and 17, dependent on an amended claim, are determined to be patentable.

New claim 46 is added and determined to be patentable.

Claims 1-12 and 18-45 were not reexamined.

13. An implantable device, the device comprising a biointerface membrane, the membrane comprising a first domain and a second domain, wherein the first domain is distal to the implantable device, wherein the first domain comprises a solid portion comprising silicone and having a plurality of interconnected cavities therein that form a cavernous configuration with greater than one cavity in three dimensions substantially throughout the entirety of the first domain, wherein the second domain is proximal to the implantable device*, wherein the second domain is resistant to cellular attachment*, and wherein the second domain is permeable to the passage of a chemical and is impermeable to cells [or] *and* cell processes.

16. [The implantable device of claim 13,] *An implantable device, the device comprising a biointerface membrane, the membrane comprising a first domain and a second domain, wherein the first domain is distal to the implantable device, wherein the first domain comprises a solid portion comprising silicone and having a plurality of interconnected cavities therein that form a cavernous configuration with greater than one cavity in three dimensions substantially throughout the entirety of the first domain, wherein the second domain is proximal to the implantable device, and wherein the second domain is permeable to the passage of a chemical and is impermeable to cells and cell processes and further* comprising a cell transplantation device.

*46. The implantable device of claim 13, further comprising an enzyme membrane, wherein the enzyme membrane comprises an enzyme configured to react with glucose.*

* * * * *